(12) United States Patent
Huang et al.

(10) Patent No.: US 8,120,765 B2
(45) Date of Patent: Feb. 21, 2012

(54) OBSERVATION DEVICE

(75) Inventors: Hongxin Huang, Hamamatsu (JP); Takashi Inoue, Hamamatsu (JP)

(73) Assignee: Hamamatsu Photonics K.K., Hamamatsu-shi, Shizuoka (JP)

( * ) Notice: Subject to any disclaimer, the term of this patent is extended or adjusted under 35 U.S.C. 154(b) by 17 days.

(21) Appl. No.: 12/866,771

(22) PCT Filed: Jan. 13, 2009

(86) PCT No.: PCT/JP2009/050320
§ 371 (c)(1),
(2), (4) Date: Aug. 9, 2010

(87) PCT Pub. No.: WO2009/101829
PCT Pub. Date: Aug. 20, 2009

(65) Prior Publication Data
US 2010/0321675 A1     Dec. 23, 2010

(30) Foreign Application Priority Data
Feb. 14, 2008  (JP) .................................. 2008-033572

(51) Int. Cl.
*G01J 1/36* (2006.01)
*G01J 1/02* (2006.01)

(52) U.S. Cl. ........ 356/217; 356/512; 356/521; 356/317; 250/201.9; 250/458.1

(58) Field of Classification Search .................. 356/217, 356/317, 318, 319, 124, 512, 521; 250/251, 250/231.11, 201.1, 201.9, 458.1; 219/121.73, 219/212.83
See application file for complete search history.

(56) References Cited

U.S. PATENT DOCUMENTS

| | | | |
|---|---|---|---|
| 6,570,143 B1 * | 5/2003 | Neil et al. .................. | 250/201.9 |
| 6,717,104 B2 * | 4/2004 | Thompson et al. ...... | 219/121.73 |
| 7,095,556 B2 * | 8/2006 | Iketaki et al. ................. | 359/385 |
| 2003/0062464 A1 * | 4/2003 | Byren et al. .............. | 250/201.9 |
| 2007/0030770 A1 * | 2/2007 | Hirai .......................... | 369/44.23 |

FOREIGN PATENT DOCUMENTS

| | | |
|---|---|---|
| JP | 2004-303827 | 10/2004 |
| JP | 2007-014569 | 1/2007 |

* cited by examiner

*Primary Examiner* — Sang Nguyen
(74) *Attorney, Agent, or Firm* — Drinker Biddle & Reath LLP

(57) ABSTRACT

An observation device 1 comprises a light source unit 10, a biaxial scanning system 20, a wavefront modulation unit 30, an optical branching unit 40, a light detection unit 50, a wavefront detection unit 60, a control unit 70, and the like. The wavefront modulation unit 30 presents a compensating phase pattern for compensating for an aberration of input light and a branching phase pattern for splitting the input light into first and second beams. The wavefront detection unit 60 receives inputted light and detects a wavefront of the inputted light. The compensating phase pattern for compensating for the wavefront aberration is feedback-controlled in loop processing that includes the detection of a wavefront distortion of the light by the wavefront detection unit 60, the adjustment of the phase pattern by the control unit 70 according to the result of detection, and the presentation of the phase pattern by the wavefront modulation unit 30.

5 Claims, 17 Drawing Sheets

Fig.8

| DIVISION RATIO($I_1/I_0$) | PHASE MODULATION DEPTH h (WAVELENGTH) |
|---|---|
| 0 | 0 |
| 0.001 | 0.002 |
| 0.005 | 0.058 |
| 0.010 | 0.086 |
| 0.020 | 0.120 |
| 0.050 | 0.182 |
| 0.100 | 0.242 |
| 0.200 | 0.312 |
| 0.500 | 0.420 |
| 0.942 | 0.500 |
| 1.00 | 0.508 |
| 2.00 | 0.596 |
| 5.00 | 0.704 |
| 10.00 | 0.774 |
| 50.80 | 0.896 |
| 99.00 | 0.930 |
| 197.60 | 0.958 |
| ∞ | 1.00 |

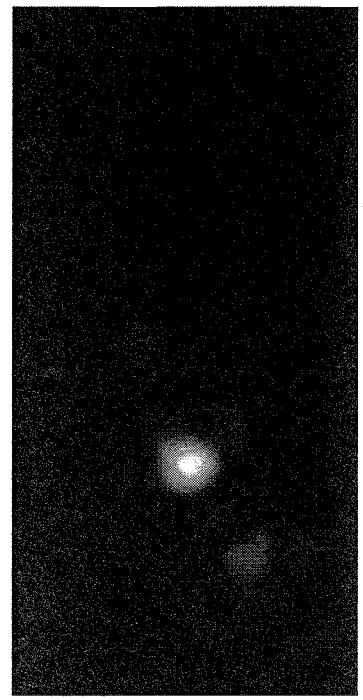 (a)
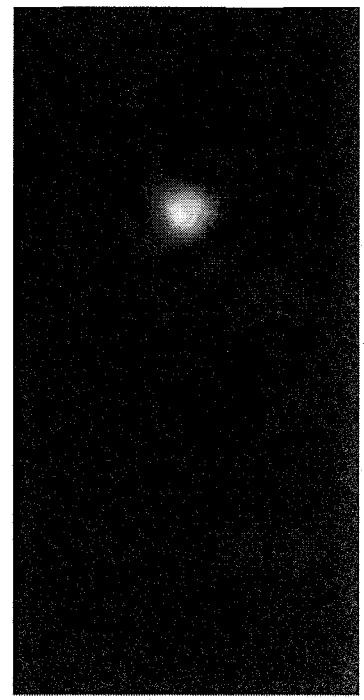 (b)
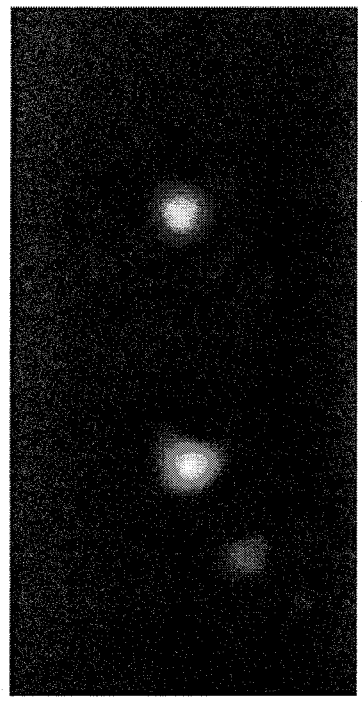 (c)
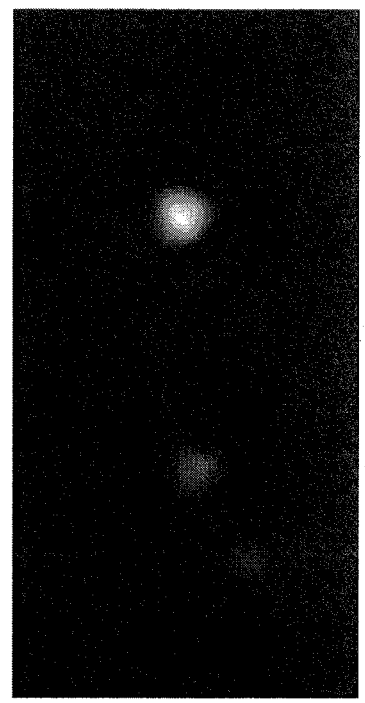 (d)
Fig. 9

OBSERVATION DEVICE

TECHNICAL FIELD

The present invention relates to an observation device.

BACKGROUND ART

Patent Literature 1 discloses an observation device (ophthalmic imaging device) which scans an eye of an examinee with a laser beam irradiation position and receives a reflected beam from the eye by a light detection unit, thereby observing the eye. In the observation device disclosed in this literature, the reflected beam from the eye is split into two by a half mirror, one of the split beams is received by the light detection unit, where its power is detected, and the other is received by a wavefront detection unit, where its wavefront aberration is detected. A wavefront modulation unit (wavefront compensation unit) compensates for the wavefront aberration of the reflected beam according to the wavefront aberration detected by the wavefront detection unit, and an image of the eye is obtained according to the light power detected by the light detection unit. The observation device disclosed in the literature is said to be able to obtain a photographed image having a high resolution by the foregoing.

In general, wavefront aberration compensation techniques including wavefront detection and wavefront modulation as mentioned above can improve image-forming characteristics and measurement accuracy. Conventionally, the wavefront aberration compensation techniques have mainly been used for astronomical telescopes. Recently, however, the wavefront aberration compensation techniques have also been coming into use for fundus cameras, scanning laser ophthalmoscopes (SLO), optical coherent tomography (OCT), laser microscopes, and the like.

Imaging using such a wavefront aberration compensation technique enables observation with a high resolution which has not conventionally been achievable. When its subject is a fundus of an eye in particular, photoreceptor cells and minute blood vessels can be observed. Observing the photoreceptor cells is useful for diagnosing age-related eye diseases. Observing the minute blood vessels is useful for early diagnosis of circulatory diseases. Therefore, a fundus imaging system using a wavefront aberration compensation technique, if commercialized, is expected to make a great impact on medical industries.

Patent Literature 1: Japanese Patent Application Laid-Open No. 2007-014569

DISCLOSURE OF INVENTION

Technical Problem

The observation device disclosed in Patent Literature 1 is provided with a half mirror which splits the reflected beam from an eye of an examinee into two in order for the light detection unit and wavefront detection unit to detect the power and wavefront aberration of the reflected beam from the eye, respectively. The branching ratio for splitting the beam into two by the half mirror has been fixed since the construction of the device and cannot be altered later.

Subjects to be measured by observation devices such as fundus cameras, SLO, and microscopes are living bodies and organisms, whereby the intensity of beams with which the subjects can be irradiated may be limited. When the subject is a fundus of an eye or the like, the reflected beam returning from the fundus becomes very weak because of low reflectance and strong scattering which are characteristics of the fundus. Splitting the beam from such a subject lowers the signal-to-noise ratio so that, in an extreme case, one or both of the wavefront aberration and image may become undetectable.

The intensity of beams returning from different subjects may vary considerably. When diagnosing complications associated with lifestyle-related diseases by fundus measurement, for example, states such as normal eyes, astigmatic eyes, lenticular abnormalities, and eye diseases vary among examinees with various light transmittances, whereby the intensity of returning beams varies greatly between individuals. When a subject has a low transmittance and a low returning beam intensity, measurement of the wavefront aberration or image may be impossible because of the insufficient exposure amount.

Since the branching ratio between the beam for detecting wavefront aberration and the beam for imaging is fixed, the measurement may become impossible or the signal-to-noise ratio may decrease when there are great differences between individual subjects as in the foregoing. Therefore, subjects that can be observed or measured by observation devices employing conventional wavefront aberration compensation techniques may be limited in some cases.

For overcoming the problems mentioned above, it is an object of the present invention to provide an observation device which can observe or measure a wide range of subjects by employing a wavefront aberration compensation technique.

Solution to Problem

The observation device in accordance with the present invention comprises (1) a light source unit for outputting light; (2) an irradiation optical system for irradiating a subject with the light outputted from the light source unit; (3) a detection optical system for guiding a beam generated upon the irradiation of the subject with the light by the irradiation optical system; (4) a wavefront modulation unit for presenting a compensating phase pattern for compensating for an aberration of input light and a branching phase pattern for splitting the input light into first and second beams, inputting the beam guided by the detection optical system, phase-modulating the inputted beam according to the compensating phase pattern and branching phase pattern, and outputting the phase-modulated beam; (5) a branching optical system for guiding the first and second beams outputted from the wavefront modulation unit while being split under action of the branching phase pattern into respective directions different from each other; (6) a light detection unit for receiving the first beam guided and inputted therein by the branching optical system and detecting a power of thus received first beam; (7) a wavefront detection unit for receiving the second beam guided and inputted therein by the branching optical system and detecting a wavefront of thus received second beam; and (8) a control unit for adjusting the compensating phase pattern presented by the wavefront modulation unit according to the wavefront detected by the wavefront detection unit, and the branching phase pattern presented by the wavefront modulation unit according to a target value for the power ratio between the first and second beams outputted from the wavefront modulation unit while being split under action of the branching phase pattern.

In the observation device in accordance with the present invention, light outputted from the light source unit irradiates the subject through the irradiation optical system. A beam generated upon the irradiation of the subject with the light by the irradiation optical system is guided to the wavefront modulation unit by the detection optical system. The wavefront modulation unit presents a compensating phase pattern for compensating for an aberration of input light and a branching phase pattern for splitting the input light into first and second beams. The beam guided by the detection optical system is inputted into the wavefront modulation unit, phase-modulated according to the compensating phase pattern and branching phase pattern, and then outputted from the wavefront modulation unit. The branching ratio between the first and second beams ranges from 1:0 to 0:1. The beam generated upon the irradiation of the subject with the light by the irradiation optical system is not limited to reflected and scattered beams, but may be any of fluorescence, Raman scattered light, second- and higher-order harmonics, and the like.

The first and second beams outputted from the wavefront modulation unit while being split under action of the branching phase pattern are guided into respective directions different from each other by the branching optical system. The first beam guided by the branching optical system so as to be fed into the light detection unit is received by the latter, whereby the power of thus received first beam is detected. The second beam guided by the branching optical system so as to be fed into the wavefront detection unit is received by the latter, whereby the wavefront of thus received second beam is detected. According to the wavefront detected by the wavefront detection unit, the control unit adjusts the compensating phase pattern presented by the wavefront modulation unit. According to a target value for the power ratio between the first and second beams outputted from the wavefront modulation unit while being split under action of the branching phase pattern, the control unit adjusts the branching phase pattern presented by the wavefront modulation unit.

Preferably, in the observation device in accordance with the present invention, the wavefront modulation unit includes a wavefront modulation element presenting a phase pattern in which the compensating phase pattern and the branching phase pattern are superimposed on each other. It is also preferable for the wavefront modulation unit to include a first wavefront modulation element for presenting the compensating phase pattern and a second wavefront modulation element for presenting the branching phase pattern.

Preferably, in the observation device in accordance with the present invention, the control unit sets the target value for the power ratio between the first and second beams outputted from the wavefront modulation unit while being split under action of the branching phase pattern according to one or both of power of the first beam received by the light detection unit and power of the second beam received by the wavefront detection unit. It is also preferable for the control unit to control a power of the light outputted from the light source unit so as to irradiate the subject through the irradiation optical system according to one or both of power of the first beam received by the light detection unit and power of the second beam received by the wavefront detection unit.

Advantageous Effects of Invention

The observation device in accordance with the present invention can observe or measure a wide range of subjects by employing a wavefront aberration compensation technique.

BRIEF DESCRIPTION OF DRAWINGS

FIG. 8 is a table illustrating a relationship between the division ratio ($I_1/I_0$) and phase modulation depth h determined by a calculation;

FIG. 9 is a chart illustrating respective converged light spots of first and second beams obtained by experiments;

REFERENCE SIGNS LIST 1 to 8 . . . observation device; 10 . . . light source unit; 11 . . . light source driver; 20 . . . biaxial scanning system; 30 to 32 . . . wavefront modulation unit; 40 . . . optical branching unit; 50 . . . light detection unit; 51 . . . pinhole; 60 . . . wavefront detection unit; 61 . . . wavefront measurement unit; 62 . . . light intensity/wavefront measurement unit; 70 to 76 . . . control unit

DESCRIPTION OF EMBODIMENTS

In the following, best modes for carrying out the present invention will be explained in detail with reference to the accompanying drawings. In the explanation of the drawings, the same constituents will be referred to with the same signs, while omitting overlapping explanations.

First Embodiment

Figure 1:
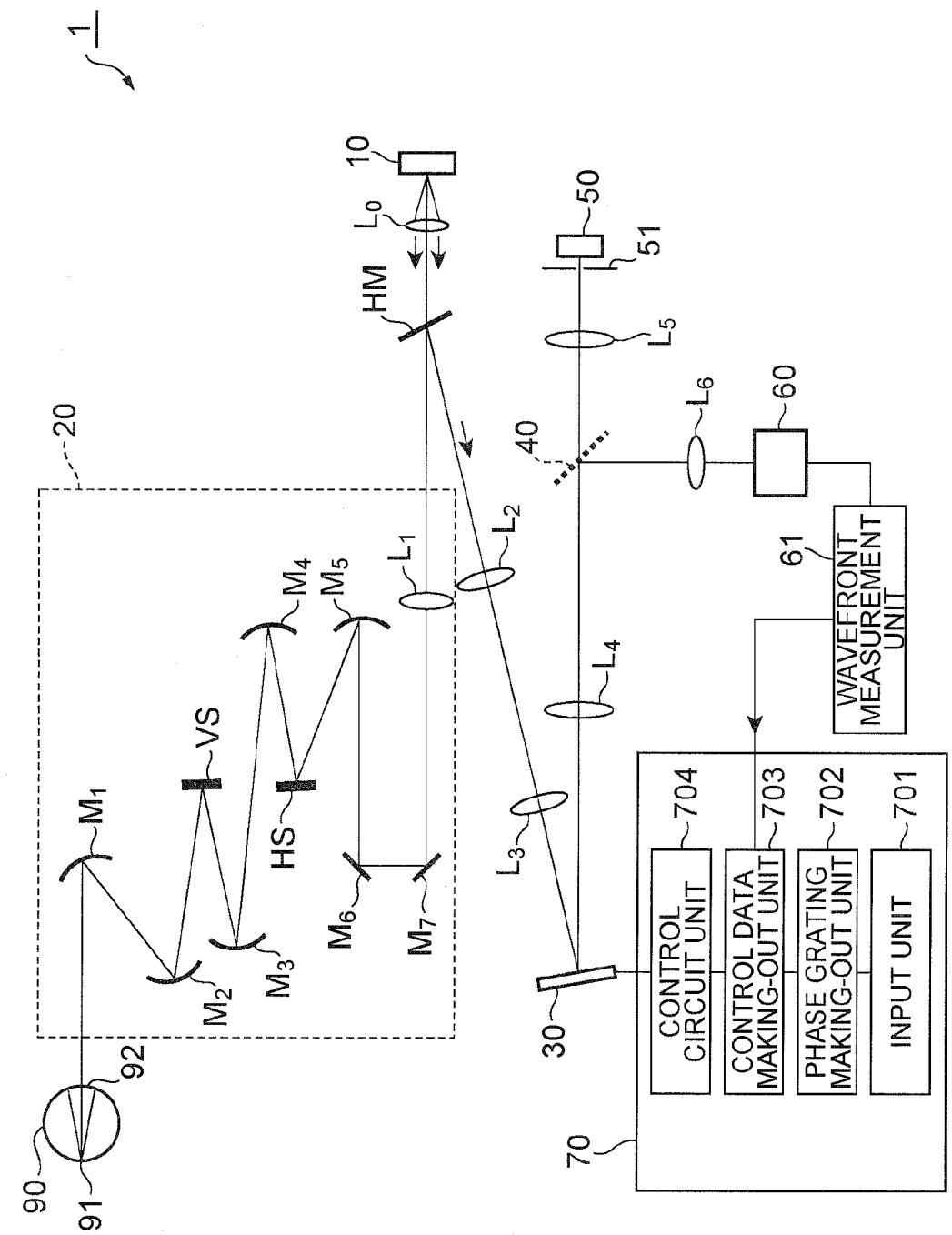
FIG. 1 is a structural diagram of an observation device 1 in accordance with a first embodiment.

To begin with, the observation device in accordance with the first embodiment will be explained. FIG. 1 is a structural diagram of the observation device 1 in accordance with the first embodiment. The observation device 1 illustrated in this diagram is a device employed in scanning-type fundus imaging for observing a fundus 91 of an eye 90 as a subject and comprises a light source unit 10, a biaxial scanning system 20, a wavefront modulation unit 30, an optical branching unit 40, a light detection unit 50, a wavefront detection unit 60, a control unit 70, and the like.

The light source unit 10 outputs light to irradiate the fundus 91 and preferably includes a light-emitting element such as a laser diode (LD) or superluminescent diode (SLD), for example, which can be regarded as a point light source. The light outputted from the light source unit 10 is collimated by a lens $L_0$ and transmitted through a half mirror HM, so as to be fed into the biaxial scanning system 20.

The biaxial scanning system 20, which irradiates the fundus 91 with the light outputted from the light source unit 10 and scans the light irradiation position, includes a lens $L_1$, mirrors $M_1$ to $M_7$, a horizontal scanning mechanism HS, and a vertical scanning mechanism VS. Each of the mirrors $M_1$ to $M_5$ has a concave reflecting surface, while each of the mirrors $M_6$ and $M_7$ has a flat reflecting surface. The light fed into the biaxial scanning system 20 from the half mirror HM travels the lens $L_1$, mirrors $M_7$, $M_6$, and $M_5$, horizontal scanning mechanism HS, mirrors $M_4$ and $M_3$, vertical scanning mechanism VS, and mirrors $M_2$ and $M_1$ in sequence, and further convergently irradiates the fundus 91 through a pupil surface 92 of the eye 90.

The light irradiation position in the fundus 91 is two-dimensionally scanned with the horizontal scanning mechanism HS and vertical scanning mechanism VS. The optical system extending from the light source unit 10 to the fundus 91 through the lens $L_0$, half mirror HM, and biaxial scanning system 20 constitutes an irradiation optical system for irradiating the subject (fundus 91) with the light outputted from the light source unit 10.

When the fundus 91 is convergently irradiated with light by biaxial scanning system 20, a reflected or scattered beam occurs at a position where the light is converged. The beam generated at the converging position in the fundus 91 is fed into the biaxial scanning system 20 through the pupil surface 92, outputted from the biaxial scanning system 20 to the half mirror HM through a route in reverse to that at the time of irradiation in the biaxial scanning system 20, and reflected by the half mirror HM, so as to be fed into the wavefront modulation unit 30 through lenses $L_2$ and $L_3$. The optical system extending from the fundus 91 to the wavefront modulation unit 30 through the biaxial scanning system 20, half mirror HM, and lenses $L_2$ and $L_3$ constitutes a detection optical system for guiding the beam generated upon the irradiation of the subject (fundus 91) with the light by the irradiation optical system to the wavefront modulation unit 30.

The wavefront modulation unit 30, which adjusts the wavefront form of input light and outputs the light after the adjustment, preferably includes a spatial light modulator of a phase modulation type. The phase-modulation-type spatial light modulator includes a plurality of pixels arranged two-dimensionally, presents a phase pattern for modulating the phase of input light at each of the plurality of pixels, and outputs the light after the phase modulation. The phase-modulation-type spatial light modulator may be either reflective or transmittable. The reflective spatial light modulator may be any of LCOS (Liquid Crystal on Silicon), MEMS (MicroElectro Mechanical Systems), or optical address types. The transmittable spatial light modulator may be an LCD (Liquid Crystal Display) or the like. FIG. 1 illustrates a phase-modulation-type reflective spatial light modulator as the wavefront modulation unit 30.

The wavefront modulation unit 30 presents a compensating phase pattern for compensating for an aberration of input light and a branching phase pattern for splitting the input light into first and second beams. In particular, the wavefront modulation unit 30 in this embodiment includes a wavefront modulation element for presenting a phase pattern in which the compensating phase pattern and the branching phase pattern are superimposed on each other. The wavefront modulation unit 30 inputs therein the beam guided by the detection optical system, phase-modulates the inputted beam according to the compensating phase pattern and branching phase pattern, and outputs the phase-modulated beam. The compensating phase pattern provides the beam with such a phase modulation as to compensate for a wavefront aberration generated during when the beam propagates through the irradiation optical system and detection optical system. On the other hand, the branching phase pattern preferably has a high light diffraction efficiency, converges the diffraction energy at specific two orders, and can control their intensity ratio, an example of which is a blazed phase diffraction grating that splits light into zero-order light and first-order diffracted light. In this case, one of the zero-order light and first-order diffracted light becomes the first beam, while the other becomes the second beam.

The first and second beams outputted from the wavefront modulation unit 30 while being split under action of the branching phase pattern pass through a lens $L_4$ and are caused to advance in respective directions different from each other by the optical branching unit 40. Of the beams outputted from the optical branching unit 40, the first beam is fed into the light detection unit 50 through a lens $L_5$ and a pinhole 51, while the second beam is fed into the wavefront detection unit 60 through a lens $L_6$. The optical system extending from the wavefront modulation unit 30 to the light detection unit 50 and wavefront detection unit 60 respectively through lens $L_4$, the optical branching unit 40 and lenses $L_5$, $L_6$ constitutes a branching optical system for guiding the first and second beams outputted from the wavefront modulation unit 30 while being split under action of the branching phase pattern into respective directions different from each other.

Here, the wavefront modulation unit 30 is disposed at a front focal position of the lens $L_4$, the optical branching unit 40 is disposed at a back focal position of the lens $L_4$, and the lens $L_4$ constitutes a Fourier transform optical system. Therefore, each of the first and second beams outputted from the wavefront modulation unit 30 is converged at the location (back focal position of the lens $L_4$) where the optical branching unit 40 is disposed. By having a reflecting part at one of the respective converging positions of the first and second beams and a transmitting part at the other, for example, the optical branching unit 40 can fully separate the first and second beams spatially from each other.

The pupil surface 92 of the eye 90, horizontal scanning mechanism HS, vertical scanning mechanism VS, wavefront modulation unit 30, and wavefront detection unit 60 are disposed at positions conjugate with each other. The fundus 91 of the eye 90, optical branching unit 40, and light detection unit 50 are also disposed at positions conjugate with each other.

The light detection unit 50 receives the first beam guided and inputted therein by the branching optical system and detects a power of thus received first beam. Preferably, the light detection unit 50 includes a photodiode. While the biaxial scanning system 20 two-dimensionally scans the light irradiation position in the fundus 91, the light detection unit 50 detects the optical power. This yields an image of the fundus 91. Here, placing the pinhole 51 at a position conjugate with the fundus 91 in front of the light detection unit 50 constructs a confocal optical system.

The wavefront detection unit 60 receives the second beam guided and inputted therein by the branching optical system and detects a wavefront of thus received second beam. Preferably, the wavefront detection unit 60 includes a Shack-Hartmann sensor, a curvature sensor, a shearing interferometer, or the like. The lenses $L_4$, $L_6$ constitute a bilateral telecentric lens system, the wavefront modulation unit 30 is disposed at the front focal position of the lens L$_4$, and the wavefront detection unit 60 is disposed at the back focal position of the lens L$_6$.

According to the wavefront of the second beam detected by the wavefront detection unit 60, the wavefront measurement unit 61 measures a wavefront distortion of the second beam. The wavefront distortion of the second beam at this time is one obtained by adding the phase modulation caused by the compensating phase pattern presented by the wavefront modulation unit 30 to the wavefront aberration generated during when the light propagates through the irradiation optical system and detection optical system, and represents an excess or deficiency in the compensation for the wavefront aberration by the compensating phase pattern.

According to the wavefront detected by the wavefront detection unit 60 and wavefront measurement unit 61, the control unit 70 adjusts the compensating phase pattern presented by the wavefront modulation unit 30 by feedback-controlling it such that the distortion of the detected wavefront becomes smaller. In response to a target value for the power ratio between the first and second beams outputted from the wavefront modulation unit 30 while being split under action of the branching phase pattern, the control unit 70 adjusts the branching phase pattern presented by the wavefront modulation unit 30.

Since the compensating phase pattern is adjusted by the feedback control in the control unit 70, the distortion of the wavefront of the second beam received by the wavefront detection unit 60 is eliminated. Since the wavefront of the first beam received by the light detection unit 50 is the same as that of the second beam received by the wavefront detection unit 60, the distortion of the wavefront of the first beam received by the light detection unit 50 is also eliminated. Therefore, the observation device 1 in accordance with this embodiment can obtain an image of the fundus 91 less influenced by the wavefront aberration. Since the power ratio of the first and second beams outputted from the wavefront modulation unit 30 while being split is set in response to the target value by the adjustment of the branching phase pattern at the control unit 70, the observation device 1 in accordance with this embodiment can observe or measure a wide range of subjects by employing a wavefront aberration compensation technique.

Examples of causes for the wavefront distortion include errors in designing and manufacturing subjects and various optical elements, their alignment errors, fluctuations due to thermal effects of media through which light passes, fluctuations in emission of the light source, and aberrations and minute movements in subjects to be measured. These lower the quality of images measured by the light detection unit 50. Eliminating the wavefront distortion by employing the wavefront aberration compensation technique can restore an image-forming characteristic, whereby fundus retinal images can be obtained with high resolution and contrast.

Figure 2:
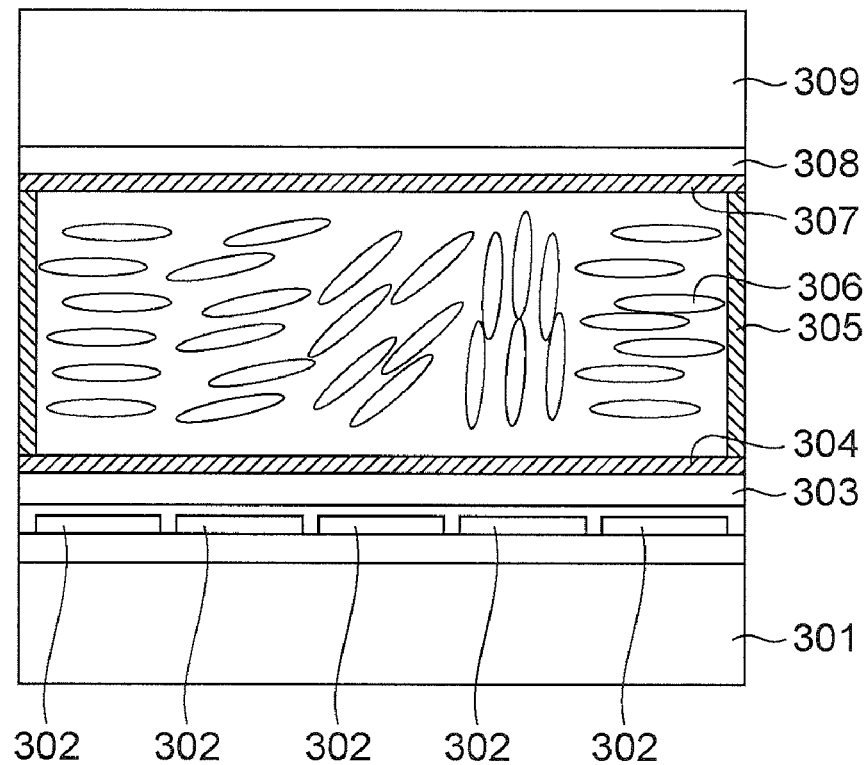
FIG. 2 is a sectional view illustrating an example of a wavefront modulation unit 30.

FIG. 2 is a sectional view illustrating an example of the wavefront modulation unit 30. This drawing depicts a spatial light modulator of the LCOS type as the wavefront modulation unit 30 and represents a cross-sectional structure corresponding to five pixels. The LCOS-type spatial light modulator as the wavefront modulation unit 30 includes a silicon substrate 301, a plurality of two-dimensionally arranged pixel electrode circuits 302, a dielectric mirror 303, an alignment film 304, spacers 305, a liquid crystal layer 306, an alignment film 307, a transparent electrode 308, and a glass substrate 309.

The gap between the alignment films 304, 307 arranged parallel to each other is closed with the spacers 305 and filled with a liquid crystal, so as to form the liquid crystal layer 306. Arranged under the alignment film 304 are the silicon substrate 301, the pixel electrode circuits 302 formed on the silicon substrate 301, and the dielectric mirror 303 disposed on the pixel electrode circuits 302. The transparent electrode 308 and glass substrate 309 are placed on the alignment film 307.

Light inputted from the upper side in this drawing passes through the glass substrate 309, transparent electrode 308, alignment film 307, liquid crystal layer 306, and alignment film 304 in sequence and then is reflected by the dielectric mirror 303. Thus reflected light passes through the alignment film 304, liquid crystal layer 306, alignment film 307, transparent electrode 308, and glass substrate 309 in sequence, so as to be outputted to the outside. The refractive index of the liquid crystal layer 306 varies depending on the voltage value applied between the transparent electrode 308 and pixel electrode circuits 302, thereby yielding different optical path lengths and different phases for the light traveling to and fro through the liquid crystal layer 306. That is, the compensating phase pattern and branching phase pattern are given as respective voltage values applied to the plurality of two-dimensionally arranged pixel electrode circuits 302.

Figure 3:
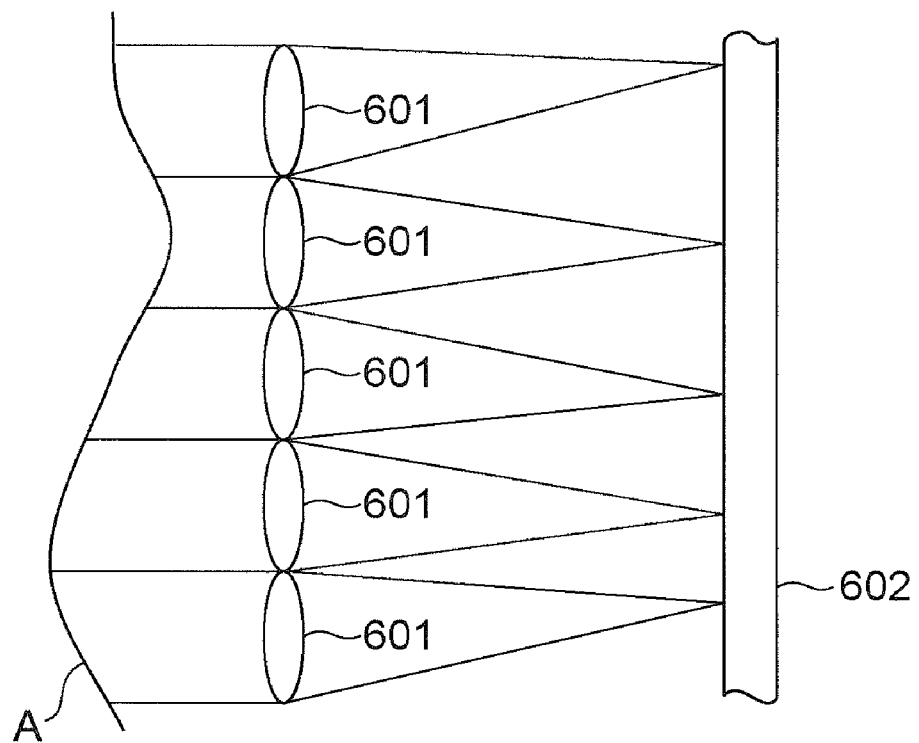
FIG. 3 is a structural diagram illustrating an example of a wavefront detection unit 60.

FIG. 3 is a structural diagram illustrating an example of a wavefront detection unit 60. This drawing represents a Shack-Hartmann sensor as the wavefront detection unit 60. The Shack-Hartmann sensor as the wavefront detection unit 60 includes a plurality of small lenses 601 and an image sensor 602. The plurality of small lenses 601 have the same structure and are arranged two-dimensionally at fixed intervals on a predetermined plane. The image sensor 602 has a light-receiving surface at the back focal plane of the plurality of small lenses 601 and outputs information concerning the respective converging positions of the plurality of small lenses 601.

When the wavefront of light inputted from the left side in this drawing is flat, the respective converging positions formed on the light-receiving surface of the image sensor 602 by the plurality of small lenses 601 are two-dimensionally arranged at fixed intervals. When the wavefront of the inputted light is not flat, however, the respective converging positions formed on the light-receiving surface of the image sensor 602 by the plurality of small lenses 601 are not arranged at fixed intervals. Hence, the distortion of the wavefront of light can be detected according to the respective converging positions formed on the light-receiving surface of the image sensor 602 by the plurality of small lenses 601.

Figure 4:
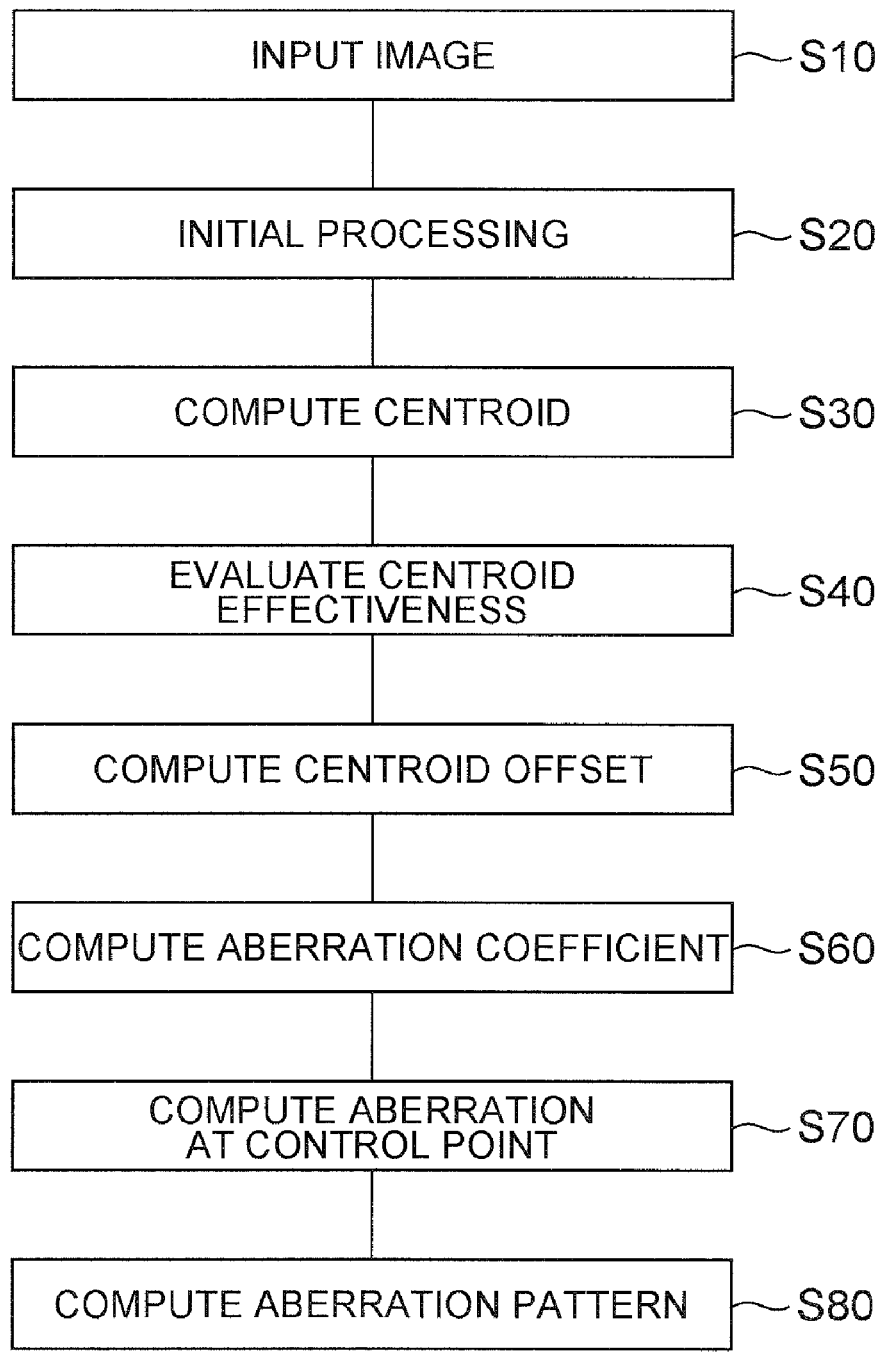
FIG. 4 is a flowchart of processing by a wavefront measurement unit 61 in the case where a Shack-Hartmann sensor is used as the wavefront detection unit 60.

The wavefront measurement unit 61 receives an output signal from the wavefront measurement unit 60, calculates a wavefront phase distribution according to the output signal, and outputs the result of calculation to the control unit 70. When a Shack-Hartmann sensor is used as the wavefront detection unit 60, the wavefront measurement unit 61 calculates the wavefront phase distribution according to an output signal, outputted from the image sensor 602 of the Shack-Hartmann sensor, indicating the converging position distribution. FIG. 4 is a flowchart of processing by the wavefront measurement unit 61 in the case where a Shack-Hartmann sensor is used as the wavefront detection unit 60. As illustrated in this chart, the wavefront measurement unit 61 inputs the output signal, outputted from the image sensor 602 of the Shack-Hartmann sensor, indicating the converging position distribution; subjects it to respective operations for initial processing, centroid computation, centroid offset computation, aberration coefficient computation, phase computation at each control point, and the like; and outputs their results to the control unit 70.

As illustrated in FIG. 1, the control unit 70 includes an input unit 701, a branching phase pattern making-out unit 702, a control data making-out unit 703, and a control circuit unit 704. The input unit 701 receives inputs of parameters necessary for making out the branching phase pattern and supplies the parameters to the branching phase pattern making-out unit 702. The branching phase pattern making-out unit 702 makes out the branching phase pattern such that the first and second beams (zero-order light and first-order diffracted light) outputted from the wavefront modulation unit 30 attain a desirable branching ratio according to the parameters received by the input unit 701 and supplies thus made branching phase pattern to the control data making-out unit 703.

The control data making-out unit 703 receives information indicating the wavefront phase distribution from the wavefront measurement unit 61 and makes out the compensating phase pattern according to this information. The control data making-out unit 703 also receives the branching phase pattern from the branching phase pattern making-out unit 702, makes out a phase pattern in which thus made compensating phase pattern and the branching phase pattern are superimposed on each other, and supplies the resulting phase pattern to the control circuit unit 704. The control circuit unit 704 receives the phase pattern from the control data making-out unit 703 and causes the wavefront modulation unit 30 to present this phase pattern.

The wavefront modulation unit 30 presenting the phase pattern in which the compensating phase pattern and branching phase pattern are superimposed on each other outputs the first and second beams that are split under action of the branching phase pattern. The first and second beams are converged at the optical branching unit 40 by the lens $L_4$ and guided to respective directions different from each other by the optical branching unit 40.

Figure 5:
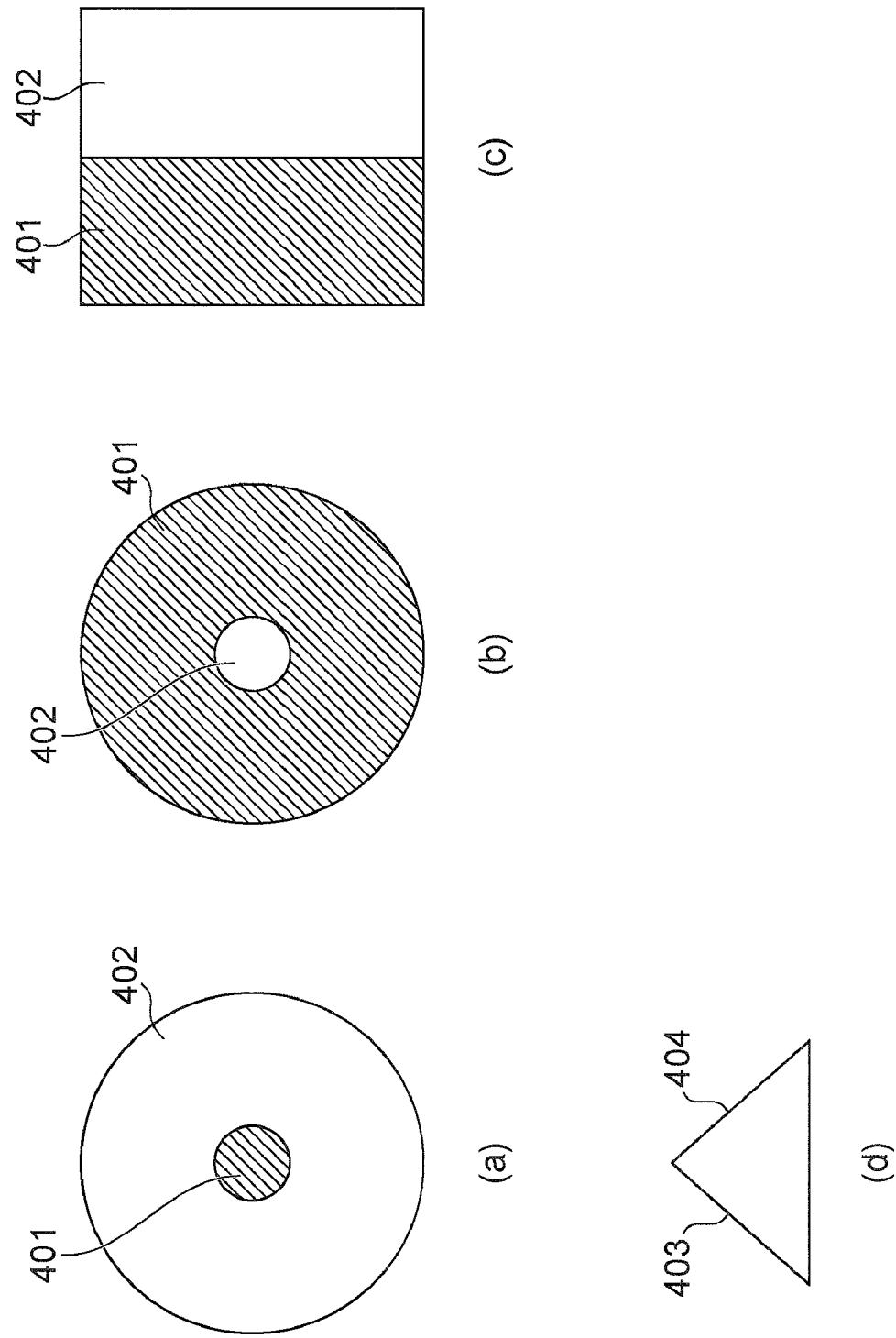
FIG. 5 is a diagram illustrating structural examples of an optical branching unit 40.

FIG. 5 is a diagram illustrating structural examples of the optical branching unit 40. The optical branching unit 40 illustrated in (a) of this drawing has a circular reflecting part 401 and a transmitting part 402 disposed about the reflecting part 401. The optical branching unit 40 illustrated in (b) of the drawing has a circular transmitting part 402 and a reflecting part 401 disposed about the transmitting part 402. The optical branching unit 40 illustrated in (c) of the drawing has a reflecting part 401 and a transmitting part 402 which are partitioned with a linear boundary. The optical branching unit 40 illustrated in (d) of the drawing is shaped like a prism whose two different surfaces are reflecting parts 403, 404.

In (a) to (c) of the drawing, the transmitting part 402 may be made of a transparent medium or no medium (an opening or the like) in particular. The optical branching unit 40 in each of the structural examples in (a) to (c) of the drawings reflects one of the first and second beams outputted from the wavefront modulation unit 30 with the reflecting part 401 and transmits the other through the transmitting part 402. The optical branching unit 40 in the structural example in (d) of the drawing reflects one of the first and second beams outputted from the wavefront modulation unit 30 with the reflecting part 403 and the other with the reflecting part 404.

A method of making out a phase pattern to be presented by the wavefront modulation unit 30 will now be explained. The phase pattern to be presented by the wavefront modulation unit 30 is made when the control data making-out unit 703 superimposes the branching phase pattern made by the branching phase pattern making-out unit 702 in the control unit 70 and the compensating phase pattern made by the control data making-out unit 703 of the control unit 70 onto each other.

The compensating phase pattern for compensating for the wavefront aberration is feedback-controlled in loop processing that includes the detection of the wavefront distortion in light by the wavefront detection unit 60, the adjustment of the phase pattern by the control unit 70 according to the result of detection, and the presentation of the phase pattern by the wavefront modulation unit 30. The compensating phase pattern $w_n(x, y)$ in the nth feedback loop is calculated by the following expression (1) according to the compensating phase pattern $w_{n-1}(x, y)$ in the (n−1)th feedback loop and the wavefront distortion $A_n(x, y)$ of light detected by the wavefront detection unit 60. Here, x and y are coordinates representing the pixel position of the wavefront modulation unit 30, which indicate positions of the pixel electrode circuits 302 when the LCOS-type spatial light modulator (FIG. 3) is used as the wavefront modulation unit 30. Also, a is the feedback coefficient.

[Math. 1]

$$w_n(x,y) = w_{n-1}(x,y) - \alpha A_n(x,y) \tag{1}$$

Figure 6:
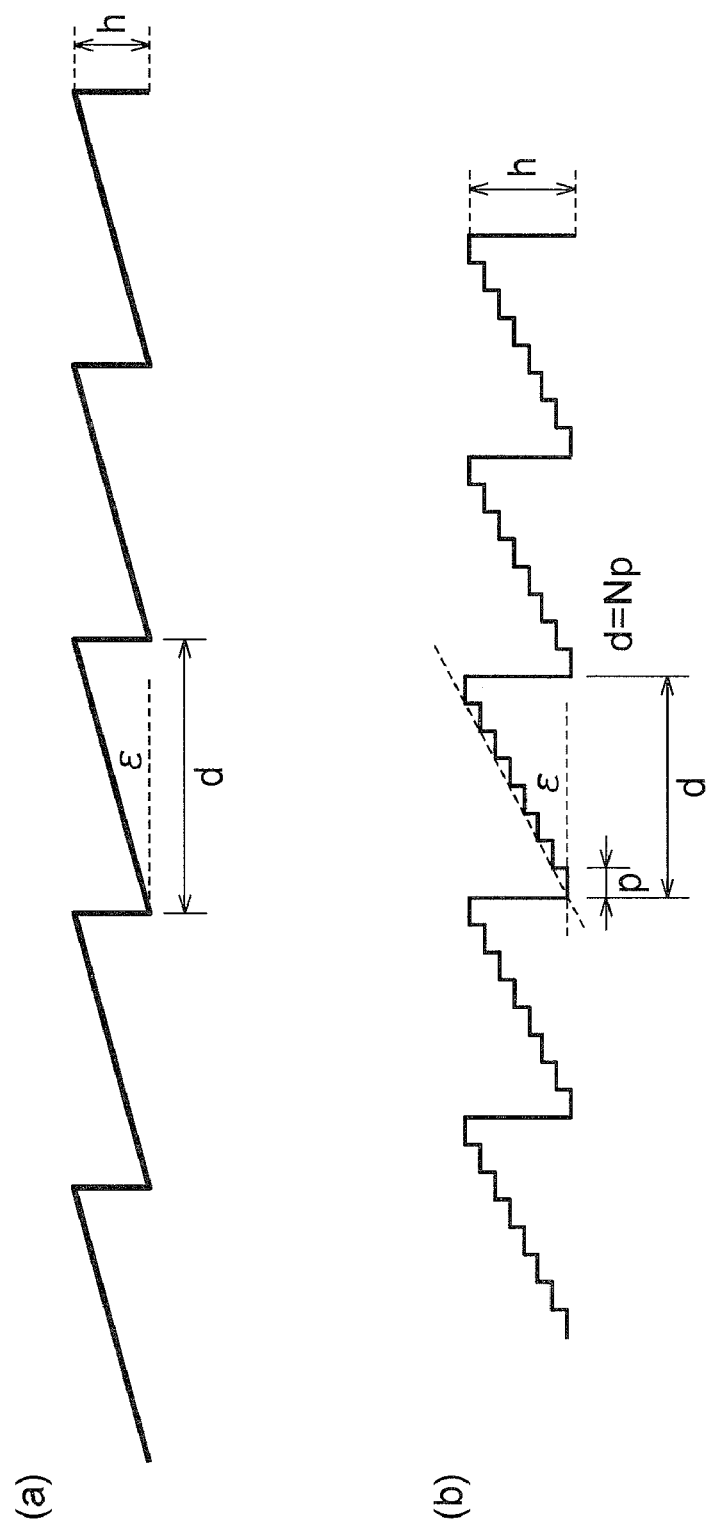
FIG. 6 is a diagram illustrating phase distribution cross sections in a blazed phase diffraction grating as a branching phase pattern.

On the other hand, the branching phase pattern for splitting the input light into the first and second beams is preferably a blazed phase diffraction grating as mentioned above. FIG. 6 is a diagram illustrating phase distribution cross sections in a blazed phase diffraction grating as a branching phase pattern. While an ideal phase distribution cross section is one illustrated in (a) of this drawing, an actual phase distribution cross section is stepped as illustrated in (b) of the drawing under the influence of the pixel structure of the wavefront modulation unit 30. The form of the blazed phase diffraction grating is uniquely determined by the grating pitch d and phase modulation depth h (or blaze angle ∈). The branching angle of the first and second beams outputted from the wavefront modulation unit 30 is determined by the grating pitch d. The power ratio between the first and second beams outputted from the wavefront modulation unit 30 is determined by the phase modulation depth h.

Figure 7:
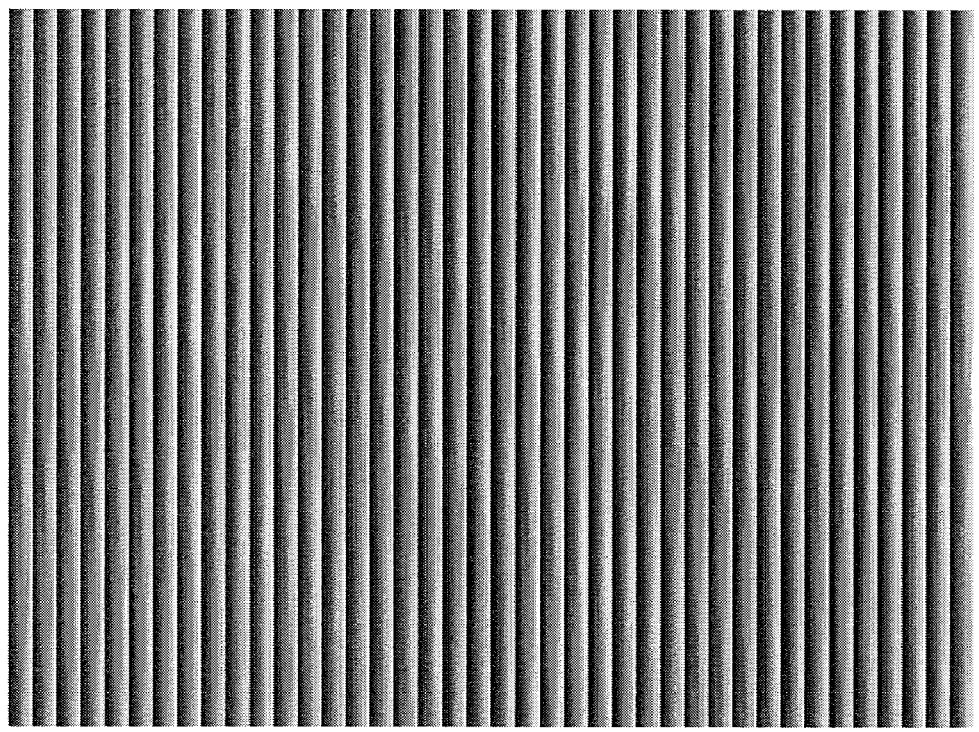
FIG. 7 is a diagram illustrating an actual example of the blazed phase diffraction grating as a branching phase pattern.

FIG. 7 is a diagram illustrating an actual example of the blazed phase diffraction grating as a branching phase pattern. In this diagram, the gradation and phase modulation depth in each pixel are supposed to be in a linear relationship, a phase modulation depth of $2\pi$ ($1\lambda$) corresponds to a gradation value of 255, and a phase modulation depth of 0 corresponds to a gradation value of 0. Phase differences exceeding $2\pi$ (corresponding to an optical path length difference exceeding one wavelength) are converted into phase values of 0 to $2\pi$ by phase wrapping and represented by gradation values after the conversion. That is, the phases within the range of 0 to $2\pi$ are normalized into an 8-bit digital gradation. Let g(x, y) be the phase distribution in thus obtained branching phase pattern.

The phase pattern to be presented by the wavefront modulation unit 30 is determined by calculations conforming to the following expressions (2) and (3). Expression (2) adds thus determined compensating phase pattern $w_n(x, y)$ and branching phase pattern g(x, y) together, thereby yielding a phase pattern S1(x, y) after the addition. Then, expression (3) performs phase wrapping, so as to determine a phase pattern s(x, y) to be presented by the wavefront modulation unit 30. Here, modulo(*, $2\pi$) is an arithmetic operation for determining the remainder after dividing by $2\pi$.

[Math. 2]

$$S1(x,y) = w_n(x,y) + g(x,y) \tag{2}$$

[Math. 3]

$$s(x,y) = \text{modulo}(S1(x,y), 2\pi) \tag{3}$$

The control circuit unit 704 included in the control unit 70 transforms thus determined phase pattern s(x, y) into a digital gradation, subjects the digital gradation to post-processing for correcting the nonlinearity of the wavefront modulation unit 30 and the like, converts the post-processed digital gradation into an analog voltage, and applies the analog voltage to each pixel (x, y) of the wavefront modulation unit 30.

The above has explained a case where parameters for the branching phase pattern are fed into the input unit 701. The branching phase pattern making-out unit 702 may read a corresponding branching phase pattern by using a lookup table method from a library of branching phase patterns which has been made for various combinations of the grading pitch d and phase modulation depth h and stored in a memory beforehand. Therefore, an index for phase gratings to be selected may be fed into the input unit 701, and the branching phase pattern making-out unit 702 may read data for a corresponding branching phase pattern from the phase grating library by using this index.

The branching phase pattern will now be explained in more details. Letting f be the focal length of the lens $L_4$, $\lambda$ be the wavelength of light, $\theta_i$ be the incidence angle of light on the wavefront modulation unit 30, $\theta_d$ be the diffraction angle in the wavefront modulation unit 30, and d be the grating pitch in the blazed phase diffraction grating as the branching phase pattern, the gap $\Delta$ between the respective converging positions of the first and second beams (zero-order light and first-order diffracted light) in the optical branching unit 40 at the back focal position of the lens $L_4$ is represented by the following expression (4):

[Math. 4]

$$\Delta = f\sin(\theta_d - \theta_i) = \frac{\lambda f}{d}\cos(\theta_i) \tag{4}$$

This expression establishes a relationship among the parameters d, $\Delta$, f, $\lambda$, and $\theta_i$. It will be sufficient if the optical branching unit 40 is designed such as to be able to isolate the first and second beams separated from each other by the gap $\Delta$. In the optical branching unit 40 having the structure illustrated in FIG. 5(a), for example, it will be sufficient if the diameter of the circular reflecting part 401 is about $\Delta$. In the optical branching unit 40 having the structure illustrated in FIG. 5(b), it will be sufficient if the diameter of the circular transmitting part 402 is about $\Delta$. In the optical branching unit 40 having the structure illustrated in FIG. 5(c), it will be sufficient if the boundary line separating the reflecting part 401 and transmitting part 402 from each other is located at the midpoint between respective converging positions of the first and second beams (zero-order light and first-order diffracted light). In the optical branching unit 40 having the structure illustrated in FIG. 5(d), it will be sufficient if the boundary line separating the reflecting parts 403, 404 from each other is located at the midpoint between respective converging positions of the first and second beams (zero-order light and first-order diffracted light).

For appropriately controlling the power ratio between the first and second beams, it is necessary for the relationship between the power ratio and the parameters of the branching phase pattern to be known beforehand. This can be determined from theoretical formulas or experimental results.

The following is a method of determining it from theoretical formulas. The intensity distribution $I(\theta)$ of diffracted light by the blazed phase diffraction grating as the branching phase pattern is represented by the following expression (5). Here, N is the number of grating periods, and A is a constant. The number of grating periods N is determined by the following expression (6) from the size D of a light beam incident on the grating surface and the grating pitch d.

[Math. 5]

$$I(\theta) = A|F_1|^2 \times |F_2|^2 \tag{5}$$

$$= A\left|\frac{\sin\left(\frac{N\pi d}{\lambda}(\sin\theta - \sin\theta_i)\right)}{N\sin\left(\frac{\pi d}{\lambda}(\sin\theta - \sin\theta_i)\right)}\right|^2 \times$$

$$\left|\frac{\sin\left(\frac{\pi}{\lambda}\left(d(\sin\theta - \sin\theta_i) + \frac{h}{2}(\cos\theta + \cos\theta_i)\right)\right)}{\frac{\pi}{\lambda}\left(d(\sin\theta - \sin\theta_i) + \frac{h}{2}(\cos\theta + \cos\theta_i)\right)}\right|^2$$

[Math. 6]

$$N = D/d \tag{6}$$

The diffraction angle of the zero-order light equals the incidence angle $\theta_i$, whereby the zero-order light intensity $I_0$ can be determined by $I(\theta_i)$. Since the diffraction angle $\theta_d$ of the first-order diffracted light is given by the above-mentioned expression (4), the intensity $I_1$ of the first-order diffracted light can be calculated by $I(\theta_d)$. By using this expression while changing the phase modulation depth h, the division ratio ($I_1/I_0$) is calculated at each phase modulation depth, so as to form a table. Using this table as a lookup table makes it possible to determine a phase modulation depth h which achieves a desirable division ratio. FIG. 8 is a table illustrating the division ratio ($I_1/I_0$) and phase modulation depth h determined by the calculation. Here, the wavelength $\lambda$ is 0.8 μm, the grating pitch d is 800 μm, the incidence angle $\theta_i$ is 10°, and the number of grating periods N is 20.

The relationship between the division ratio ($I_1/I_0$) and phase modulation depth h can also be determined by experiments. A phase grating having a grating pitch d and a phase modulation depth h is fed into the wavefront modulation unit 30, the respective intensities of the zero-order light and first-order light are measured by a power meter, and their power ratio is calculated. Blazed phase diffraction gratings are made with different modulation depths h and fed into the wavefront modulation unit 30, and the above-mentioned measurement and calculation are repeated. Then, the relationship between the measured power ratios and phase modulation depths h is formed into a table.

Experimental results will now be set forth. FIG. 9 is a chart illustrating the respective converged light spots of the first and second beams obtained by experiments. Here, a CCD camera was disposed in place of the optical branching unit 40 and captured the respective converged light spots of the first and second beams. In each of (a) to (d) in this drawing, the left and right images are the respective converged light spots of the zero-order light and first-order diffracted light. The blaze angle $\in$ of the blazed phase diffraction grating as the branching phase pattern is varied among (a) to (d) in the drawing.

In the drawing, (b) illustrates an image in the case where the phase modulation depth h is 0 (the blaze angle $\in$ is 0), in which the optical energy distributed to the first-order diffracted light is the smallest while the optical energy distributed to the zero-order light is the largest. In the drawing, (d) illustrates an image in the case where the phase modulation depth h is $\lambda$ (the blaze angle $\in$ is $\lambda/d$), in which the optical energy distributed to the zero-order light is the smallest while the optical energy distributed to the first-order diffracted light is the largest. In the drawing, (a) and (c) represent images between the above-mentioned cases, in which the optical energy is distributed to both of the zero-order light and first-order diffracted light.

The images obtained by the experiments illustrated in FIG. 9 incur wavefront aberration, so that each converged light spot is widened instead of being a diffraction-limited spot. However, their intensity distributions are seen to be similar to each other and have the same aberration.

The foregoing explanation illustrates an embodiment in which the observation device 1 is employed for scanning-type fundus imaging. Replacing the human eye and the subject with an objective lens and a biological sample, respectively, constructs a scanning laser microscope. That is, substantially the same structure as that of FIG. 1 is formed when the present invention is employed in the scanning laser microscope.

Second Embodiment

Figure 10:
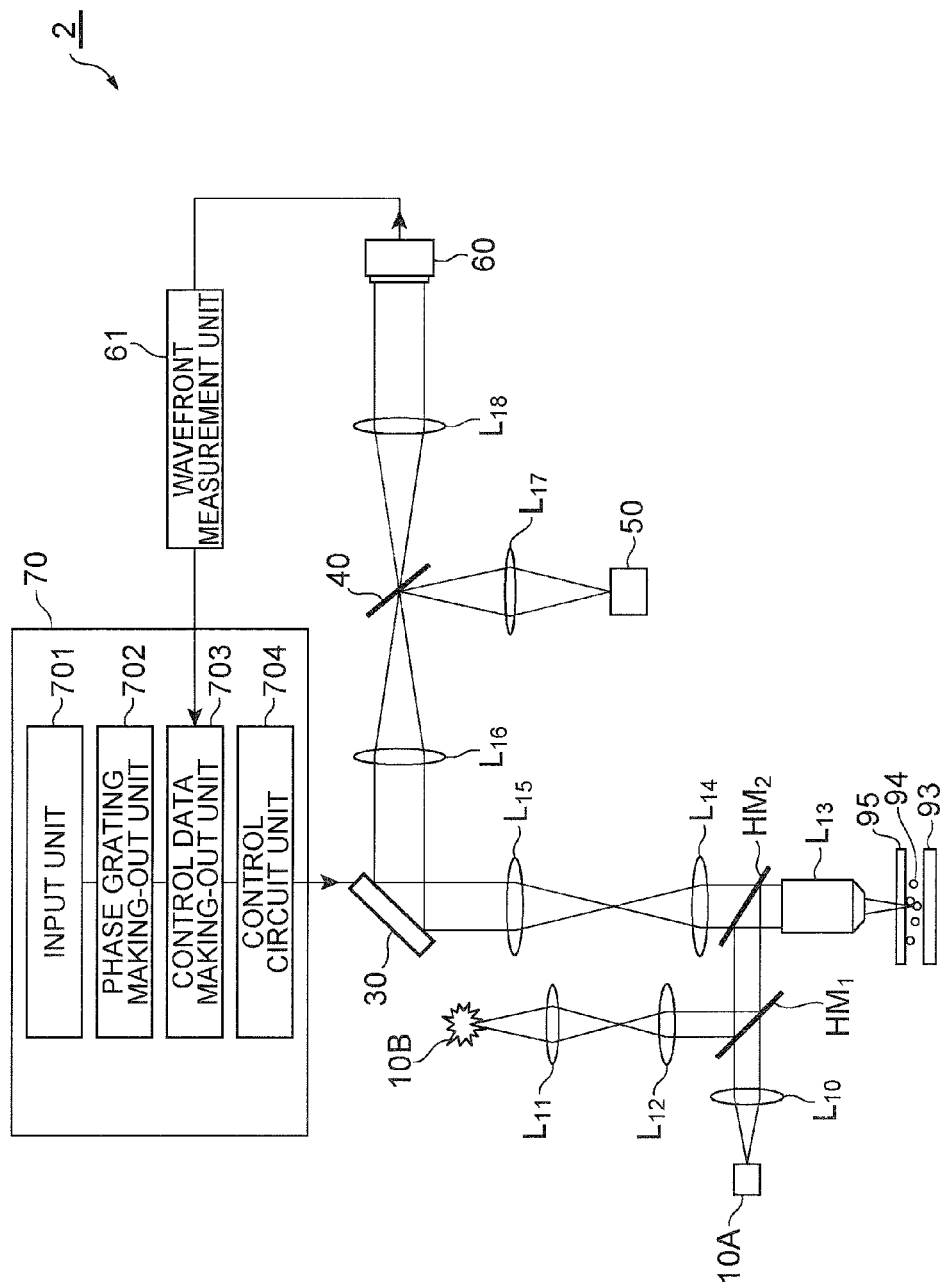
FIG. 10 is a structural diagram of an observation device 2 in accordance with a second embodiment.

The observation device in accordance with the second embodiment will now be explained. FIG. 10 is a structural diagram of an observation device 2 in accordance with the second embodiment. The observation device 2 illustrated in this drawing is a device employed in a biological microscope for observing a biological sample 94 placed as a subject on a stage 93 and comprises light source units 10A, 10B, a wavefront modulation unit 30, an optical branching unit 40, a light detection unit 50, a wavefront detection unit 60, a control unit 70, and the like.

For protecting the biological sample 94 as the subject placed on the stage 93, a cover glass sheet 95 covers the biological sample 94. The cover glass sheet 95 also causes a wavefront distortion in light, which makes it necessary to compensate for the wavefront of light by using a wavefront aberration compensation technique. In this embodiment, the compensation for the wavefront of light is followed by an observation of the biological sample 94.

The wavefront modulation unit 30 is disposed at a front focal position of a lens $L_{16}$, the optical branching unit 40 is disposed at a back focal position of the lens $L_{16}$, and the $L_{16}$ constitutes a Fourier transform optical system. Therefore, each of the first and second beams outputted from the wavefront modulation unit 30 is converged at the location (back focal position of the lens $L_{16}$) where the optical branching unit 40 is disposed. By having a reflecting part at one of the respective converging positions of the first and second beams and a transmitting part at the other, for example, the optical branching unit 40 can fully separate the first and second beams spatially from each other.

Light is outputted from one light source unit 10A of the two when compensating for the wavefront of light and from the other light source unit 10B when observing the biological sample 94. While a phase pattern in which a compensating phase pattern and a branching phase pattern are superimposed on each other is presented by the wavefront modulation unit 30, the branching phase pattern is set such that the light outputted from the wavefront modulation unit 30 is transmitted through the optical branching unit 40 and received by the wavefront detection unit 60 when compensating for the wavefront of light and such that the light outputted from the wavefront modulation unit 30 is reflected by the optical branching unit 40 and received by the light detection unit 50 when observing the biological sample 94.

When compensating for the wavefront of light, the light outputted from the light source unit 10A is collimated by a lens $L_{10}$, transmitted through a half mirror $HM_1$, reflected by a half mirror $HM_2$, converged by an objective lens $L_{13}$, and passed through the cover glass sheet 95, so as to irradiate the biological sample 94. The light (reflected light, scattered light, or the like) generated by the biological sample 94 upon the irradiation is passed through the cover glass sheet 95, collimated by an objective lens $L_{13}$, transmitted through a half mirror $HM_2$, and fed into the wavefront modulation unit 30 through lenses $L_{14}$, $L_{15}$. The light fed into the wavefront modulation unit 30 has its wavefront aberration compensated for by the compensating phase pattern presented by the wavefront modulation unit 30 and is outputted as light advancing in a specific direction according to the branching phase pattern presented by the wavefront modulation unit 30. The light outputted from the wavefront modulation unit 30 is transmitted through the optical branching unit 40 through the lens $L_{16}$ and received by the wavefront detection unit 60 through a lens $L_{18}$. The compensating phase pattern for compensating for the wavefront aberration is feedback-controlled in loop processing that includes the detection of the wavefront distortion in light by the wavefront detection unit 60, the adjustment of the phase pattern by the control unit 70 according to the result of detection, and the presentation of the phase pattern by the wavefront modulation unit 30.

When observing the biological sample 94, on the other hand, the light outputted from the light source unit 10B is collimated by lenses $L_{11}$, $L_{12}$, reflected by the half mirror $HM_1$, converged by an objective lens $L_{13}$, and passed through the cover glass sheet 95, so as to irradiate the biological sample 94. The light (reflected light, scattered light, or the like) generated by the biological sample 94 upon the irradiation is passed through the cover glass sheet 95, collimated by the objective lens $L_{13}$, transmitted through the half mirror $HM_2$, and fed into the wavefront modulation unit 30 through the lenses $L_{14}$, $L_{15}$. The light fed into the wavefront modulation unit 30 has its wavefront aberration compensated for by the compensating phase pattern presented by the wavefront modulation unit 30 and is outputted as light advancing in a direction different from the above-mentioned specific direction according to the branching phase pattern presented by the wavefront modulation unit 30. The light outputted from the wavefront modulation unit 30 is passed through the lens $L_{16}$, reflected by the optical branching unit 40, and received by the light detection unit 50 through a lens $L_{17}$. The biological sample 94 is observed as the light detection unit 50 receives the light.

Thus, without mechanically movable parts, this embodiment adjusts the branching phase pattern presented by the wavefront modulation unit 30, whereby the light outputted from the light source units 10A, 10B is selectively guided to one of the light detection unit 50 and wavefront detection unit 60 and can efficiently be utilized for any of the wavefront detection and image detection.

Third Embodiment

Figure 11:
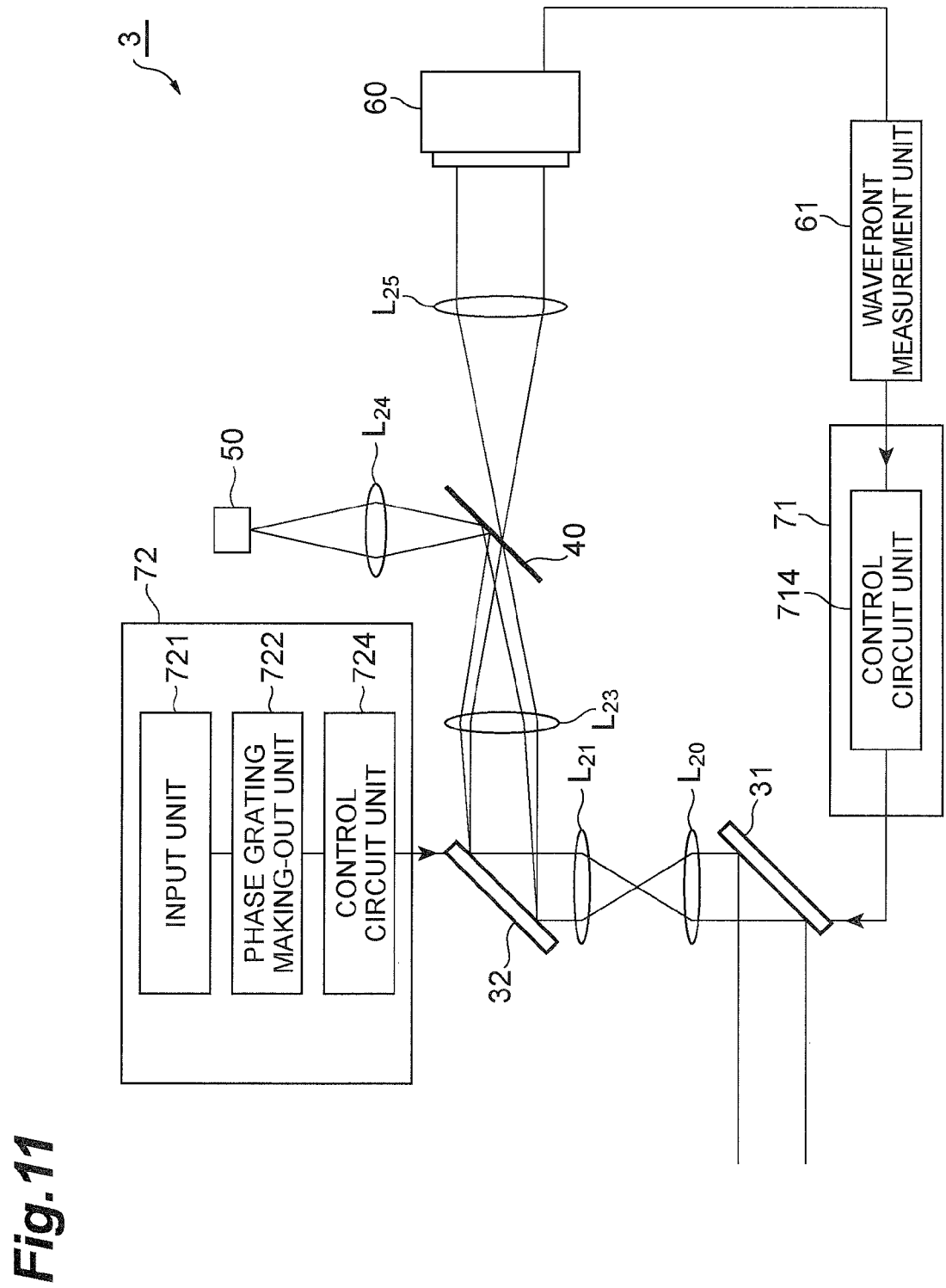
FIG. 11 is a structural diagram of an observation device 3 in accordance with a third embodiment.

The observation device in accordance with the third embodiment will now be explained. FIG. 11 is a structural diagram of an observation device 3 in accordance with the third embodiment. The observation device 3 illustrated in this drawing comprises a light source unit, first and second wavefront modulation elements 31, 32 as wavefront modulation units, an optical branching unit 40, a light detection unit 50, a wavefront detection unit 60, control units 71, 72, and the like. This drawing does not depict the structure extending from the light source unit to the first wavefront modulation element 31 through a subject.

The first wavefront modulation element 31 presents a compensating phase pattern for compensating for the wavefront distortion of light. The second wavefront modulation element 32 presents a branching phase pattern for splitting the input light into first and second beams. Lenses $L_{30}$, $L_{31}$ are disposed on an optical path between the first and second wavefront modulation elements 31, 32 that are positioned optically conjugate with each other.

The wavefront modulation element 32 is disposed at a front focal position of a lens $L_{23}$, the optical branching unit 40 is disposed at a back focal position of the lens $L_{23}$, and the $L_{23}$ constitutes a Fourier transform optical system. Therefore, each of the first and second beams outputted from the wavefront modulation unit 30 is converged at the location (back focal position of the lens $L_{23}$) where the optical branching unit 40 is disposed. By having a reflecting part at one of the respective converging positions of the first and second beams and a transmitting part at the other, for example, the optical branching unit 40 can fully separate the first and second beams spatially from each other.

A control circuit unit 714 included in the control unit 71 receives information indicating a wavefront phase distribution from the wavefront measurement unit 61, makes out a compensating phase pattern according to this information, and causes the first wavefront modulation element 31 to present this compensating phase pattern.

An input unit 721 included in the control unit 72 receives inputs of parameters necessary for making out the branching phase pattern and supplies the parameters to a branching phase pattern making-out unit 722. The branching phase pattern making-out unit 722 makes out the branching phase pattern such that the first and second beams (zero-order light and first-order diffracted light) outputted from the second wavefront modulation element 32 attain a desirable branching ratio according to the parameters received by the input unit 721 and supplies thus made branching phase pattern to a control circuit unit 724. The control circuit unit 724 causes the second wavefront modulation element 32 to present this phase pattern.

In the observation device 3 in accordance with this embodiment, the light generated by the subject has its first wavefront modulation element compensated for by the compensating phase pattern presented by the first wavefront modulation element 31, passes through lenses $L_{21}$, $L_{22}$, and is split into the first and second beams by the branching phase pattern presented by the second wavefront modulation element 32 positioned conjugate with the first wavefront modulation element 31.

The first and second beams outputted from the second wavefront modulation element 32 while being split under action of the branching phase pattern are passed through the lens $L_{23}$ and caused to advance in respective directions different from each other by the optical branching unit 40. Of the light outputted from the optical branching unit 40, the first beam is fed into the light detection unit 50 through a lens $L_{24}$, while the second beam is fed into the wavefront detection unit 60 through a lens $L_{25}$.

The compensating phase pattern for compensating for the wavefront aberration is feedback-controlled in loop processing that includes the detection of the wavefront distortion in light by the wavefront detection unit 60, the adjustment of the phase pattern by the control unit 71 according to the result of detection, and the presentation of the phase pattern by the first wavefront modulation element 31. The subject is observed as the light detection unit 50 receives the light.

The observation device 3 in accordance with this embodiment includes two wavefront modulation elements 31, 32 as wavefront modulation units, which complicate optical systems and increase the device scale, but has the following advantages. The first wavefront modulation element 31 for compensation is required to have a high response speed in order to raise the compensation accuracy. The second wavefront modulation element 32 for splitting is demanded less for high response speed but more for high spatial resolution. In general, the response speed of the wavefront modulation unit is lower as the number of pixels is greater. Therefore, one having a smaller number of pixels but a higher response speed is used as the first wavefront modulation element 31 for compensation, while one having a lower response speed but a greater number of pixels is used as the second wavefront modulation element 32 for splitting. Thus employing optimal ones as the wavefront modulation elements 31, 32 according to their respective required performances can improve the measurement speed and measurement accuracy.

Fourth Embodiment

Figure 12:
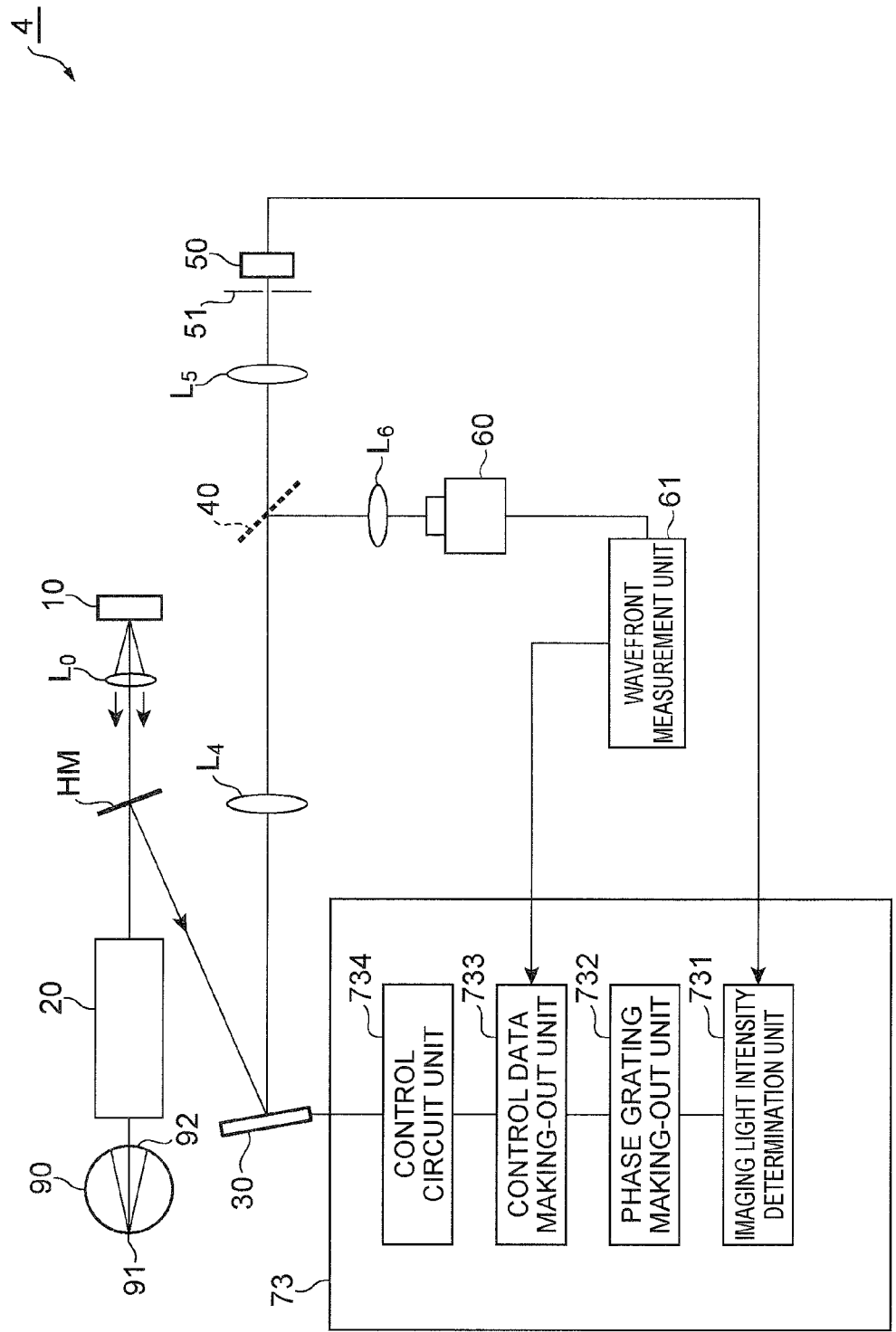
FIG. 12 is a structural diagram of an observation device 4 in accordance with a fourth embodiment.

The observation device in accordance with the fourth embodiment will now be explained. FIG. 12 is a structural diagram of an observation device 4 in accordance with the fourth embodiment. The observation device 4 in accordance with the fourth embodiment illustrated in FIG. 12 differs from the structure of the observation device 1 in accordance with the first embodiment illustrated in FIG. 1 in that it has a control unit 73 instead of the control unit 70.

According to the wavefront detected by the wavefront detection unit 60 and wavefront measurement unit 61, the control unit 73 adjusts the compensating phase pattern presented by the wavefront modulation unit 30 by feedback-controlling it such that the distortion of the detected wavefront becomes smaller. The control unit 73 also sets a target value for the power ratio between the first and second beams outputted from the wavefront modulation unit 30 while being split under action of the branching phase pattern and adjusts the branching phase pattern presented by the wavefront modulation unit 30 according to this target value.

The control unit 73 includes an imaging light intensity determination unit 731, a branching phase pattern making-out unit 732, a control data making-out unit 733, and a control circuit unit 734. The imaging light intensity determination unit 731 receives a signal indicating the result of detection of an optical power by the light detection unit 50, determines whether the optical power falls within an appropriate range or not, and supplies the result of determination to the branching phase pattern making-out unit 732. The branching phase pattern making-out unit 732 determines a target value for the branching ratio between the first and second beams (zero-order light and first-order diffracted light) outputted from the wavefront modulation unit 30 such that the power of the light received by the light detection unit 50 falls within the appropriate range according to the result of determination by the imaging light intensity determination unit 731, makes out such a branching phase pattern as to yield this branching ratio, and supplies thus made branching phase pattern to the control data making-out unit 733.

The control data making-out unit 733 receives information indicating a wavefront phase distribution from the wavefront measurement unit 61 and makes out a compensating phase pattern according to this information. The control data making-out unit 733 also receives the branching phase pattern from the branching phase pattern making-out unit 732, makes out a phase pattern in which thus made compensating phase pattern and the branching phase pattern are superimposed on each other, and supplies the resulting phase pattern to the control circuit unit 734. The control circuit unit 734 receives the phase pattern from the control data making-out unit 733 and causes the wavefront modulation unit 30 to present the phase pattern.

Thus, the observation device 4 in accordance with this embodiment can set the branching phase pattern presented by the wavefront modulation unit 30 such that the power of light received by the light detection unit 50 falls within an appropriate range, thereby making it possible to observe subjects at a fixed quality even when light is reflected by the subjects with various levels.

Fifth Embodiment

Figure 13:
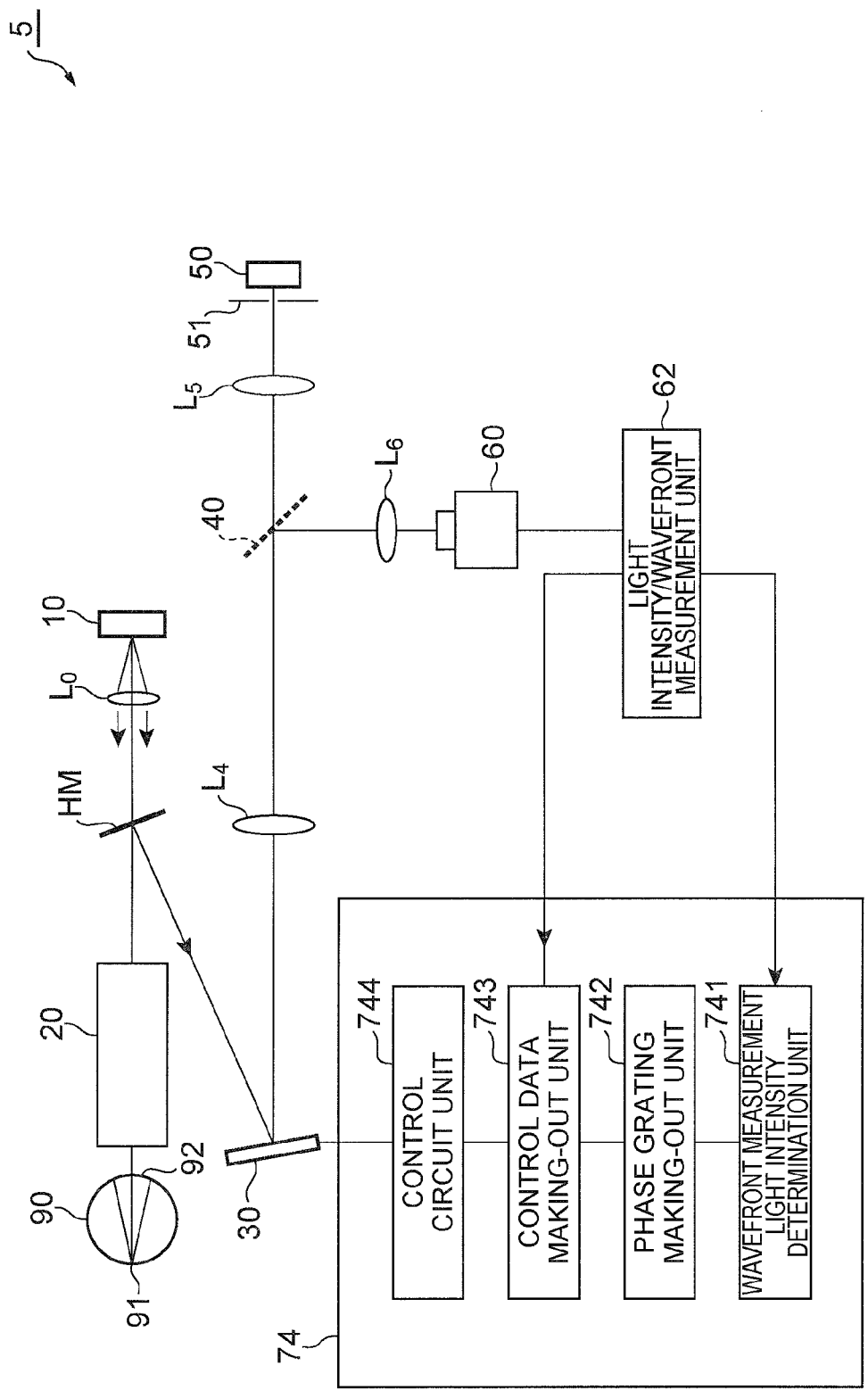
FIG. 13 is a structural diagram of an observation device 5 in accordance with a fifth embodiment.

The observation device in accordance with the fifth embodiment will now be explained. FIG. 13 is a structural diagram of an observation device 5 in accordance with the fifth embodiment. The observation device 5 in accordance with the fifth embodiment illustrated in FIG. 13 differs from the structure of the observation device 1 in accordance with the first embodiment illustrated in FIG. 1 in that it has a light intensity/wavefront measurement unit 62 and a control unit 74 instead of the wavefront measurement unit 61 and control unit 70, respectively.

Figure 14:
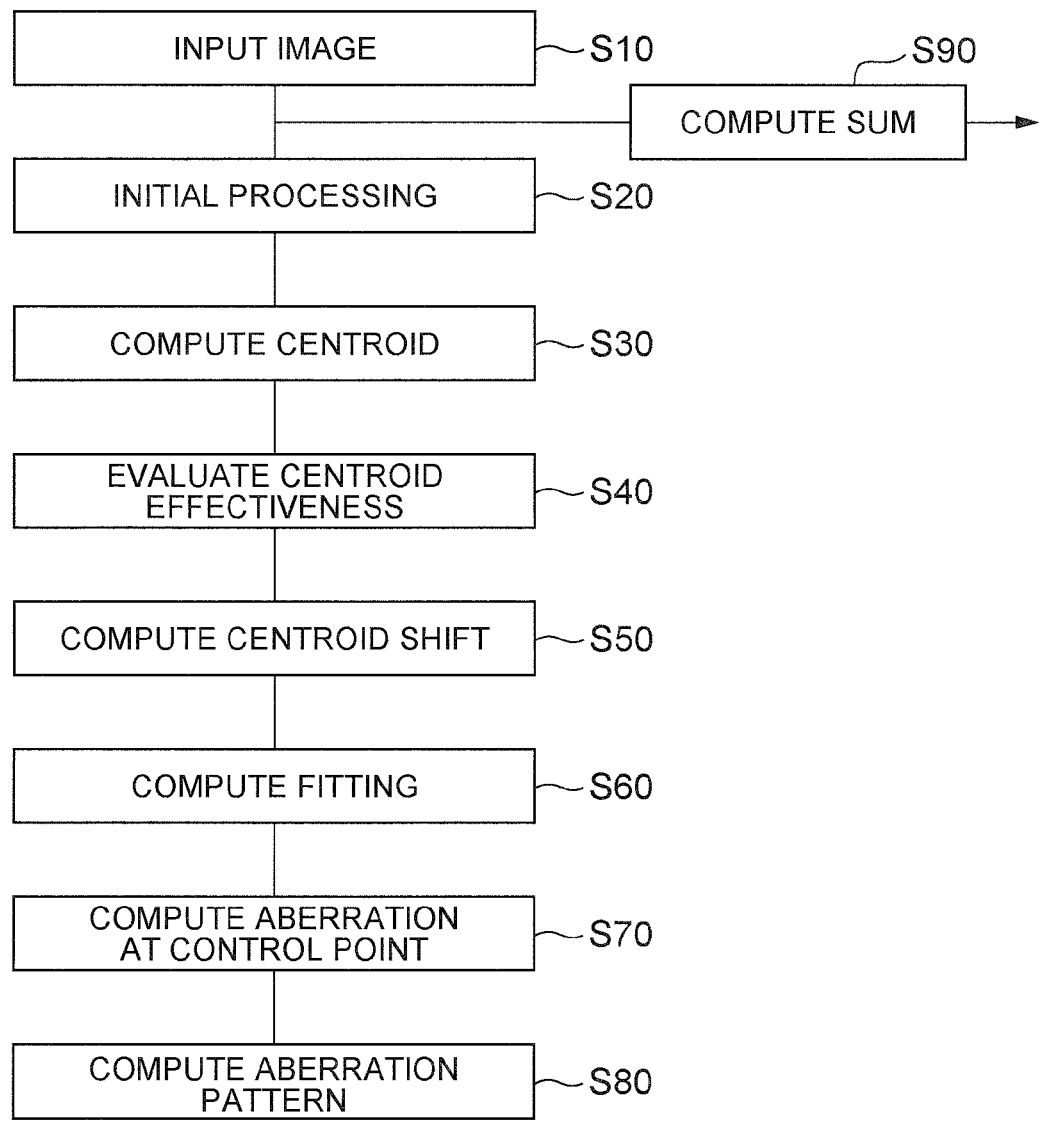
FIG. 14 is a flowchart of processing by a light intensity/wavefront measurement unit 62 in the case where a Shack-Hartmann sensor is used as the wavefront detection unit 60.

The light intensity/wavefront measurement unit 62 measures the wavefront distortion of the second beam according to the wavefront of the second beam detected by the wavefront detection unit 60 and the intensity of the second beam detected by the wavefront detection unit 60. FIG. 14 is a flowchart of processing by the light intensity/wavefront measurement unit 62 in the case where a Shack-Hartmann sensor is used as the wavefront detection unit 60. As illustrated in this chart, the light intensity/wavefront measurement unit 62 inputs the output signal, outputted from the image sensor 602 of the Shack-Hartmann sensor, indicating the converging position distribution; subjects it to respective operations for initial processing, centroid computation, centroid offset computation, aberration coefficient computation, phase computation at each control point, and the like; and outputs their results to the control unit 74. The light intensity/wavefront measurement unit 62 also adds the respective optical powers at the converging positions outputted from the image sensor 602 of the Shack-Hartmann sensor and outputs the result of addition to the control unit 74.

According to the wavefront detected by the wavefront detection unit 60 and light intensity/wavefront measurement unit 62, the control unit 74 adjusts the compensating phase pattern presented by the wavefront modulation unit 30 by feedback-controlling it such that the distortion of the detected wavefront becomes smaller. The control unit 74 also sets a target value for the power ratio between the first and second beams outputted from the wavefront modulation unit 30 while being split under action of the branching phase pattern and adjusts the branching phase pattern presented by the wavefront modulation unit 30 according to this target value.

The control unit 74 includes a wavefront measurement light intensity determination unit 741, a branching phase pattern making-out unit 742, a control data making-out unit 743, and a control circuit unit 744. The wavefront measurement light intensity determination unit 741 receives a signal indicating the result of detection of an optical power by the light intensity/wavefront measurement unit 62, determines whether the optical power falls within an appropriate range or not, and supplies the result of determination to the branching phase pattern making-out unit 742. The branching phase pattern making-out unit 742 determines a target value for the branching ratio between the first and second beams (zero-order light and first-order diffracted light) outputted from the wavefront modulation unit 30 such that the power of the light received by the wavefront detection unit 60 falls within the appropriate range according to the result of determination by the wavefront measurement light intensity determination unit 741, makes out such a branching phase pattern as to yield this branching ratio, and supplies thus made branching phase pattern to the control data making-out unit 743.

The control data making-out unit 743 receives information indicating a wavefront phase distribution from the light intensity/wavefront measurement unit 62 and makes out a compensating phase pattern according to this information. The control data making-out unit 743 also receives the branching phase pattern from the branching phase pattern making-out unit 742, makes out a phase pattern in which thus made compensating phase pattern and the branching phase pattern are superimposed on each other, and supplies the resulting phase pattern to the control circuit unit 744. The control circuit unit 744 receives the phase pattern from the control data making-out unit 743 and causes the wavefront modulation unit 30 to present the phase pattern.

Thus, the observation device 5 in accordance with this embodiment can set the branching phase pattern presented by the wavefront modulation unit 30 such that the power of light received by the wavefront detection unit 60 falls within an appropriate range, thereby making it possible to observe subjects at a fixed quality even when light is reflected by the subjects with various levels.

Sixth Embodiment

Figure 15:
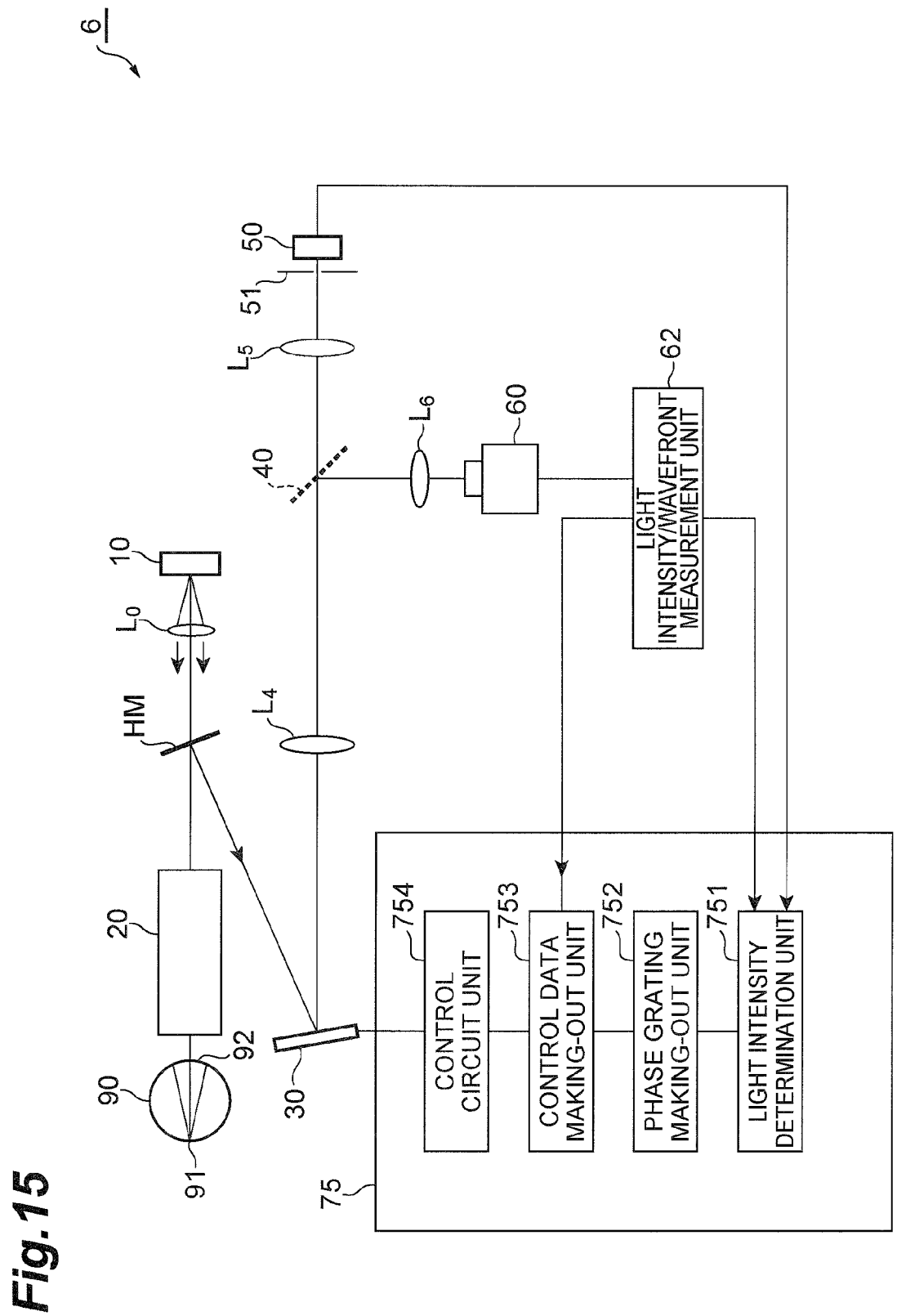
FIG. 15 is a structural diagram of an observation device 6 in accordance with a sixth embodiment.

The observation device in accordance with the sixth embodiment will now be explained. FIG. 15 is a structural diagram of an observation device 6 in accordance with the sixth embodiment. The observation device 6 in accordance with the sixth embodiment illustrated in FIG. 15 differs from the structure of the observation device 5 in accordance with the fifth embodiment illustrated in FIG. 13 in that it has a control unit 75 instead of the control unit 74.

According to the wavefront detected by the wavefront detection unit 60 and wavefront measurement unit 62, the control unit 75 adjusts the compensating phase pattern presented by the wavefront modulation unit 30 by feedback-controlling it such that the distortion of the detected wavefront becomes smaller. The control unit 75 also sets a target value for the power ratio between the first and second beams outputted from the wavefront modulation unit 30 while being split under action of the branching phase pattern and adjusts the branching phase pattern presented by the wavefront modulation unit 30 according to this target value.

The control unit 75 includes a light intensity determination unit 751, a branching phase pattern making-out unit 752, a control data making-out unit 753, and a control circuit unit 754. The light intensity determination unit 751 receives a signal indicating the result of detection of an optical power by the light detection unit 50 and a signal indicating the result of detection of an optical power by the light intensity/wavefront measurement unit 62, determines whether these optical powers fall within an appropriate range or not, and supplies the result of determination to the branching phase pattern making-out unit 752. The branching phase pattern making-out unit 752 determines a target value for the branching ratio between the first and second beams (zero-order light and first-order diffracted light) outputted from the wavefront modulation unit 30 such that the power of the light received by the light detection unit 50 or wavefront detection unit 60 falls within the appropriate range according to the result of determination by the light intensity determination unit 751, makes out such a branching phase pattern as to yield this branching ratio, and supplies thus made branching phase pattern to the control data making-out unit 753.

The control data making-out unit 753 receives information indicating a wavefront phase distribution from the wavefront measurement unit 62 and makes out a compensating phase pattern according to this information. The control data making-out unit 753 also receives the branching phase pattern from the branching phase pattern making-out unit 752, makes out a phase pattern in which thus made compensating phase pattern and the branching phase pattern are superimposed on each other, and supplies the resulting phase pattern to the control circuit unit 754. The control circuit unit 754 receives the phase pattern from the control data making-out unit 753 and causes the wavefront modulation unit 30 to present the phase pattern.

Thus, the observation device 6 in accordance with this embodiment can set the branching phase pattern presented by the wavefront modulation unit 30 such that the power of light received by the light detection unit 50 or wavefront detection unit 60 falls within an appropriate range, thereby making it possible to observe subjects at a fixed quality even when light is reflected by the subjects with various levels.

Seventh Embodiment

Figure 16:
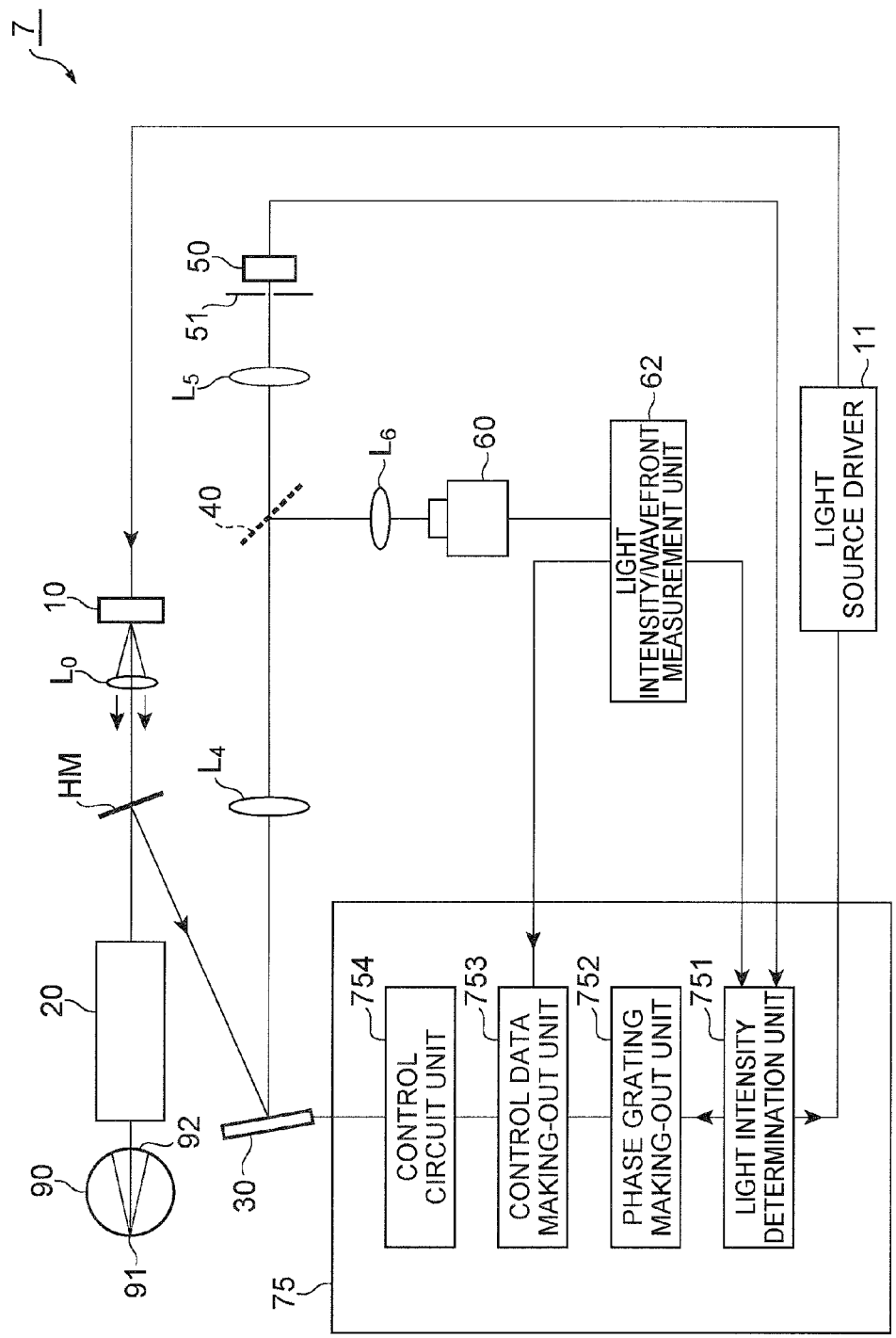
FIG. 16 is a structural diagram of an observation device 7 in accordance with a seventh embodiment.

The observation device in accordance with the seventh embodiment will now be explained. FIG. 16 is a structural diagram of an observation device 7 in accordance with the seventh embodiment. The observation device 7 in accordance with the seventh embodiment illustrated in FIG. 16 differs from the structure of the observation device 6 in accordance with the sixth embodiment illustrated in FIG. 15 in that it further comprises a light source driver 11.

The light source driver 11 drives the light source unit 10 under the control of the light intensity determination unit 751 included in the control unit 75, so as to adjust the power of light outputted from the light source unit 10. When the power of reflected light from a subject is extremely small, for example, both imaging and wavefront detection may fail. In this case, imaging is tried to perform alone after doing only the wavefront detection. If this trial fails, the intensity of light outputted from the light source unit 10 is gradually increased by the light source driver 11. Thus, even when the level of reflected light from a subject is low, the imaging and wavefront detection can be done, whereby the amount of exposure of the subject to light can be minimized.

When the level of reflected light from the subject is sufficient while the respective light-receiving powers for imaging and wavefront detection are enough, by contrast, the amount of exposure of the subject to light can be reduced as the intensity of light outputted from the light source unit 10 is made lower by the light source driver 11.

Eighth Embodiment

Figure 17:
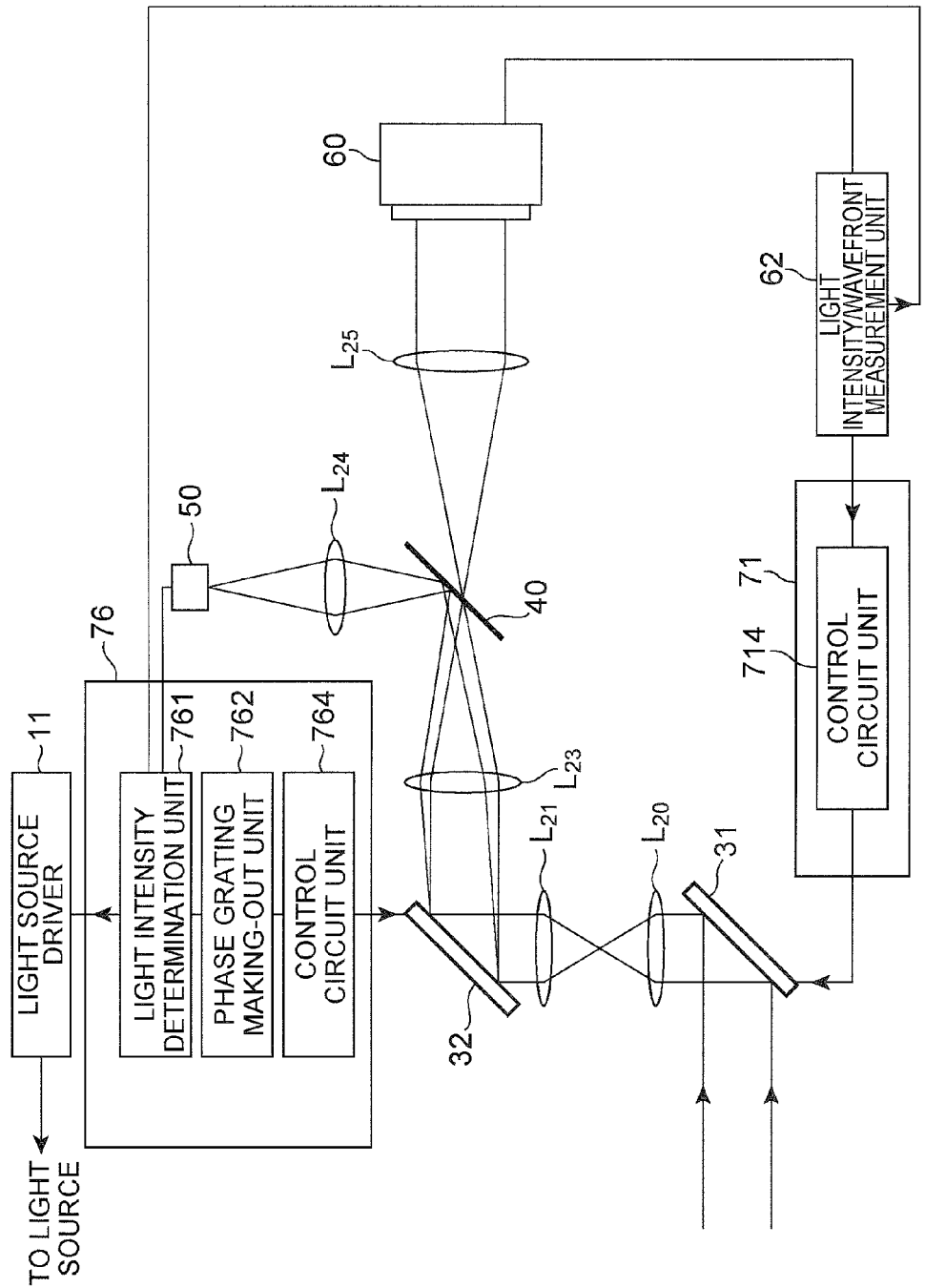
FIG. 17 is a structural diagram of an observation device 8 in accordance with an eighth embodiment.

The observation device in accordance with the eighth embodiment will now be explained. FIG. 17 is a structural diagram of an observation device 8 in accordance with the eighth embodiment. The observation device 8 in accordance with the eighth embodiment illustrated in FIG. 17 differs from the structure of the observation device 3 in accordance with the third embodiment illustrated in FIG. 11 in that it has a light intensity/wavefront measurement unit 62 and a control unit 76 instead of the wavefront measurement unit 61 and the control unit 72, respectively, and further comprises a light source driver 11.

The light intensity/wavefront measurement unit 62 measures the wavefront distortion of the second beam according to the wavefront of the second beam detected by the wavefront detection unit 60 and the intensity of the second beam detected by the wavefront detection unit 60.

The control unit 76 includes an imaging light intensity determination unit 761, a branching phase pattern making-out unit 762, and a control circuit unit 764. The light intensity determination unit 761 receives a signal indicating the result of detection of an optical power by the light detection unit 50 and a signal indicating the result of detection of an optical power by the light intensity/wavefront measurement unit 62, determines whether these optical powers fall within an appropriate range or not, and supplies the result of determination to the branching phase pattern making-out unit 762. The branching phase pattern making-out unit 762 determines a target value for the branching ratio between the first and second beams (zero-order light and first-order diffracted light) outputted from the wavefront modulation unit 30 such that the power of the light received by the light detection unit 50 or wavefront detection unit 60 falls within the appropriate range according to the result of determination by the light intensity determination unit 761, makes out such a branching phase pattern as to yield this branching ratio, and supplies thus made branching phase pattern to the control circuit unit 764. The control circuit unit 764 causes the second wavefront modulation element 32 to present this phase pattern.

The light source driver 11 drives the light source unit 10 under the control of the light intensity determination unit 761 included in the control unit 76, so as to adjust the power of light outputted from the light source unit 10.

INDUSTRIAL APPLICABILITY

The present invention provides an observation device which can observe or measure a wide range of subjects by employing a wavefront aberration compensation technique.

The invention claimed is:
1. An observation device comprising:
a light source unit for outputting light;
an irradiation optical system for irradiating a subject with the light outputted from the light source unit;
a detection optical system for guiding a beam generated upon the irradiation of the subject with the light by the irradiation optical system;
a wavefront modulation unit for presenting a compensating phase pattern for compensating for an aberration of input light and a branching phase pattern for splitting the input light into first and second beams, inputting the beam guided by the detection optical system, phase-modulating the inputted beam according to the compensating phase pattern and branching phase pattern, and outputting the phase-modulated beam;
a branching optical system for guiding the first and second beams outputted from the wavefront modulation unit while being split under action of the branching phase pattern into respective directions different from each other;
a light detection unit for receiving the first beam guided and inputted therein by the branching optical system and detecting a power of thus received first beam;

a wavefront detection unit for receiving the second beam guided and inputted therein by the branching optical system and detecting a wavefront of thus received second beam; and a control unit for adjusting the compensating phase pattern presented by the wavefront modulation unit according to the wavefront detected by the wavefront detection unit, and the branching phase pattern presented by the wavefront modulation unit according to a target value for the power ratio between the first and second beams outputted from the wavefront modulation unit while being split under action of the branching phase pattern.

2. An observation device according to claim 1, wherein the wavefront modulation unit includes a wavefront modulation element presenting a phase pattern in which the compensating phase pattern and the branching phase pattern are superimposed on each other.

3. An observation device according to claim 1, wherein the wavefront modulation unit includes a first wavefront modulation element for presenting the compensating phase pattern and a second wavefront modulation element for presenting the branching phase pattern.

4. An observation device according to claim 1, wherein the control unit sets the target value for the power ratio between the first and second beams outputted from the wavefront modulation unit while being split under action of the branching phase pattern according to one or both of power of the first beam received by the light detection unit and power of the second beam received by the wavefront detection unit.

5. An observation device according to claim 1, wherein the control unit controls a power of the light outputted from the light source unit so as to irradiate the subject through the irradiation optical system according to one or both of power of the first beam received by the light detection unit and power of the second beam received by the wavefront detection unit.

* * * * *